United States Patent
Konakanchi et al.

(10) Patent No.: US 10,604,505 B2
(45) Date of Patent: Mar. 31, 2020

(54) MODIFIED PROCESS FOR THE PREPARATION OF CERITINIB AND AMORPHOUS FORM OF CERITINIB

(71) Applicant: NATCO PHARMA LIMITED, Banjara Hills, Hyderabad (IN)

(72) Inventors: Durga Prasad Konakanchi, Hyderabad (IN); Subba Rao Pula, Hyderabad (IN); Muni Bhaskar Pallooru, Hyderabad (IN); Radha Rani Samatham, Hyderabad (IN); Ramakrishna Pilli, Hyderabad (IN); Lakshmana Viswa Venkata Pavan Kumar Maddula, Hyderabad (IN); Sandeep Karnam, Hyderabad (IN); Pulla Reddy Muddasani, Hyderabad (IN); Kali Satya Bhujanga Rao Adibhatla, Hyderabad (IN); Venkaiah Chowdary Nannapaneni, Hyderabad (IN)

(73) Assignee: Natco Pharma Limited, Banjara Hills, Hyderabad (IN)

( * ) Notice: Subject to any disclaimer, the term of this patent is extended or adjusted under 35 U.S.C. 154(b) by 0 days.

(21) Appl. No.: 16/085,240

(22) PCT Filed: Mar. 9, 2017

(86) PCT No.: PCT/IN2017/050086
§ 371 (c)(1),
(2) Date: Sep. 14, 2018

(87) PCT Pub. No.: WO2017/158619
PCT Pub. Date: Sep. 21, 2017

(65) Prior Publication Data
US 2019/0047983 A1      Feb. 14, 2019

(30) Foreign Application Priority Data

Mar. 15, 2016   (IN) .............................. 201641008975

(51) Int. Cl.
*C07D 401/12*          (2006.01)
(52) U.S. Cl.
CPC ........ *C07D 401/12* (2013.01); *C07B 2200/13* (2013.01)
(58) Field of Classification Search
CPC .................................................... C07D 401/12
See application file for complete search history.

(56) References Cited

U.S. PATENT DOCUMENTS 8,039,479 B2   10/2011  Michellys
9,309,229 B2   4/2016   Feng

FOREIGN PATENT DOCUMENTS

EP            2990405        3/2016

*Primary Examiner* — Emily A Bernhardt
(74) *Attorney, Agent, or Firm* — Vos-IP, LLC

(57) ABSTRACT

The present invention is related to an improved process for the preparation of Ceritinib with high yield and high purity. The present process is cost effective and feasible in large scale production also. The present invention also related to a stable amorphous form of Ceritinib and its preparation. The present invention also relates to a process for the preparation of Crystalline form A of Ceritinib.

7 Claims, 5 Drawing Sheets

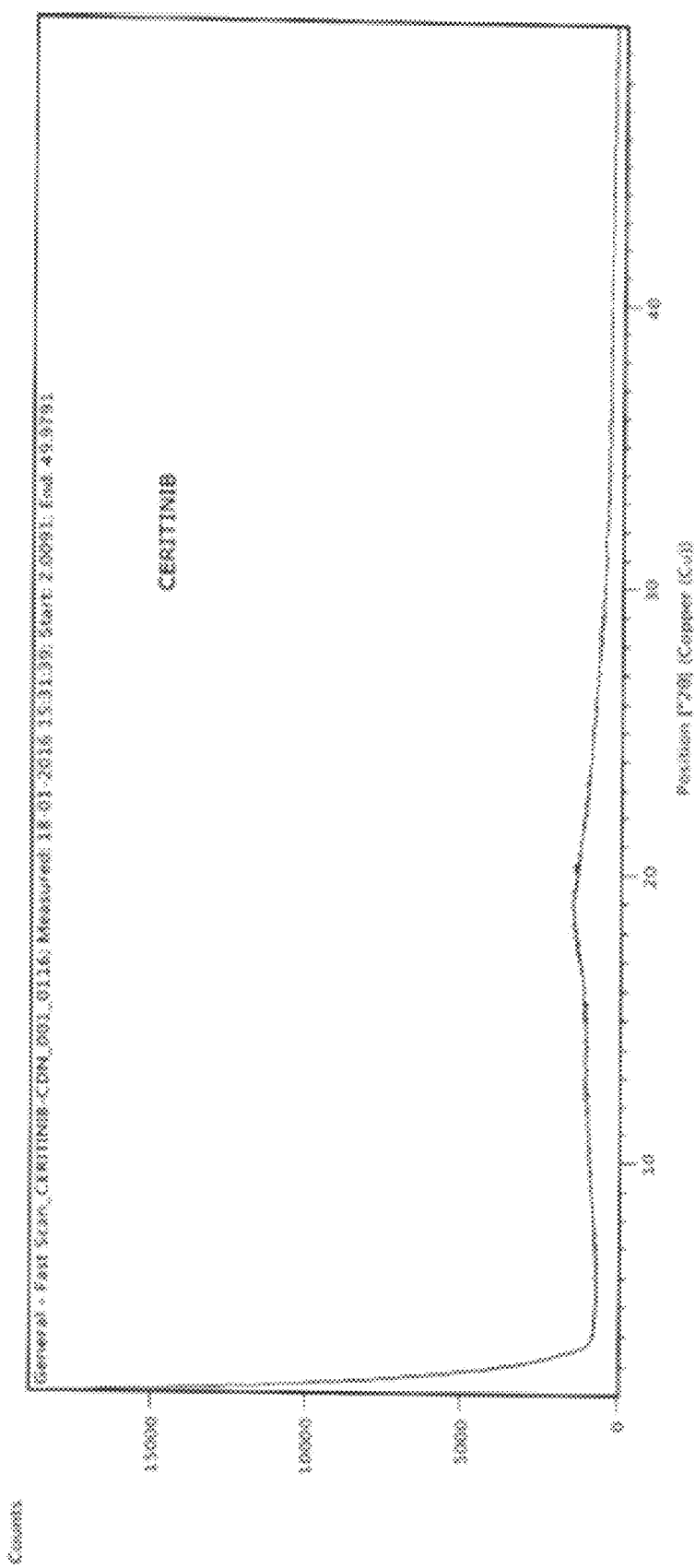
Fig-1: Powder X-ray diffractogram of an amorphous form of ceritinib.

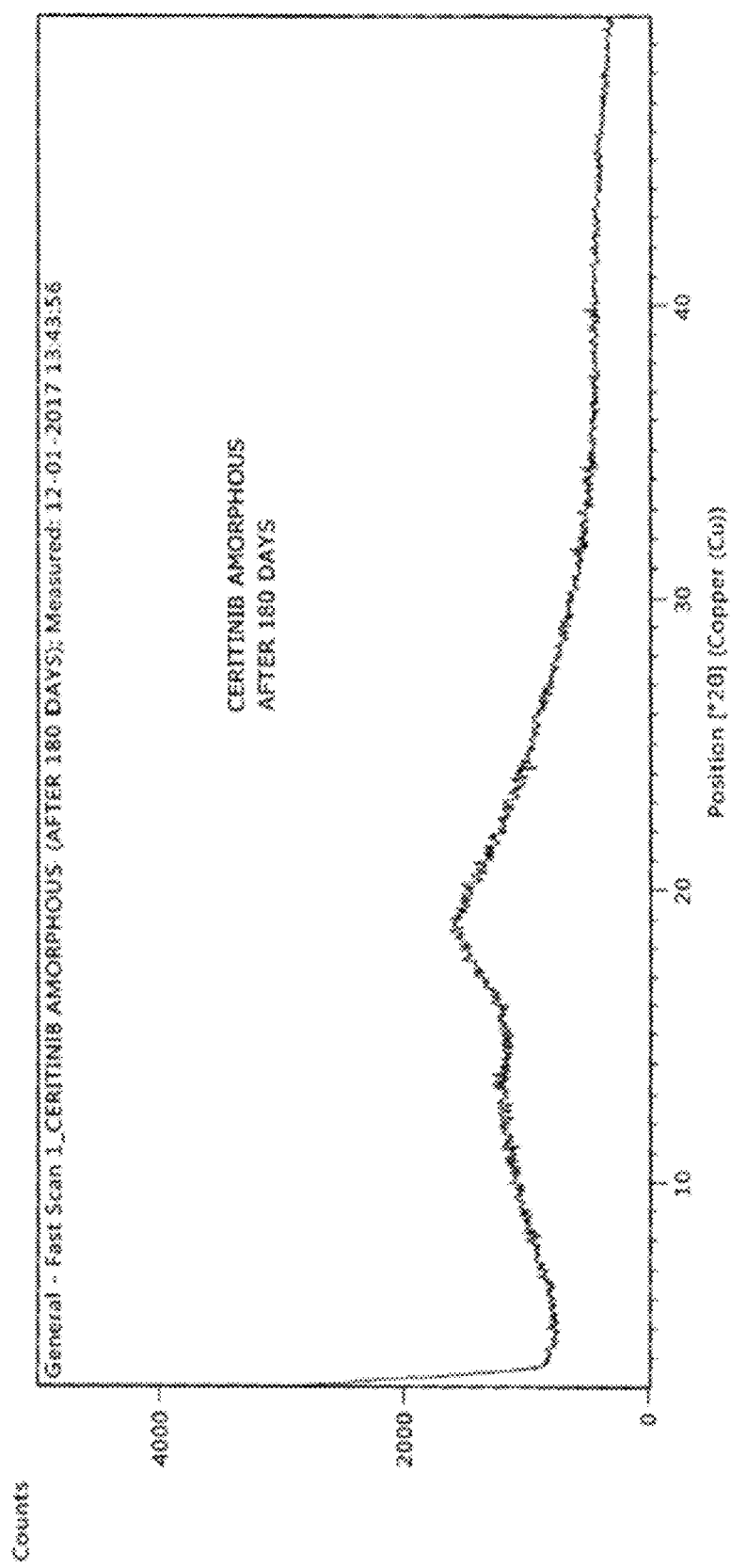
Fig.-2: Powder X-ray diffractogram of an amorphous form of ceritinib of 180days

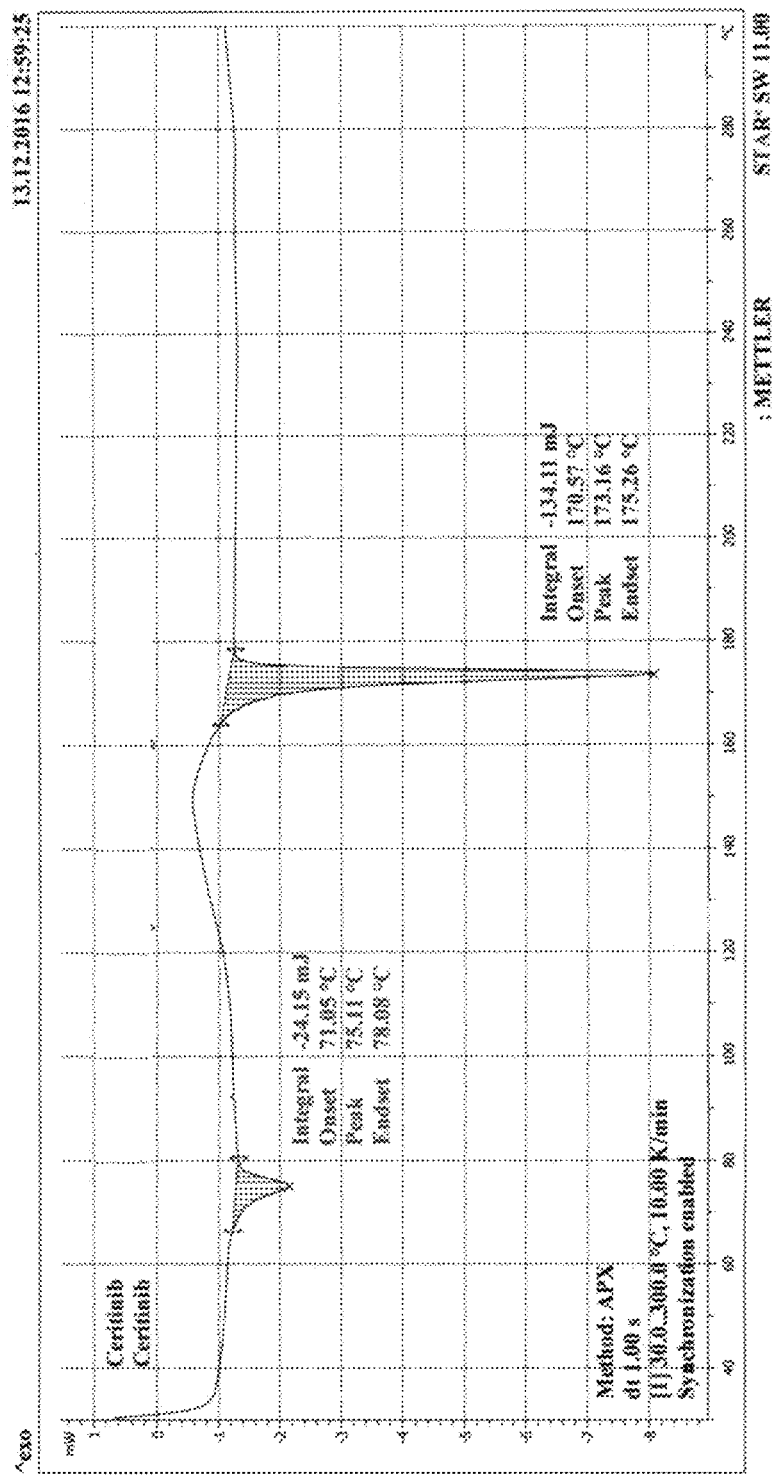
Fig-3: Differential scanning calorimetry (DSC) pattern of an amorphous form of ceritinib.

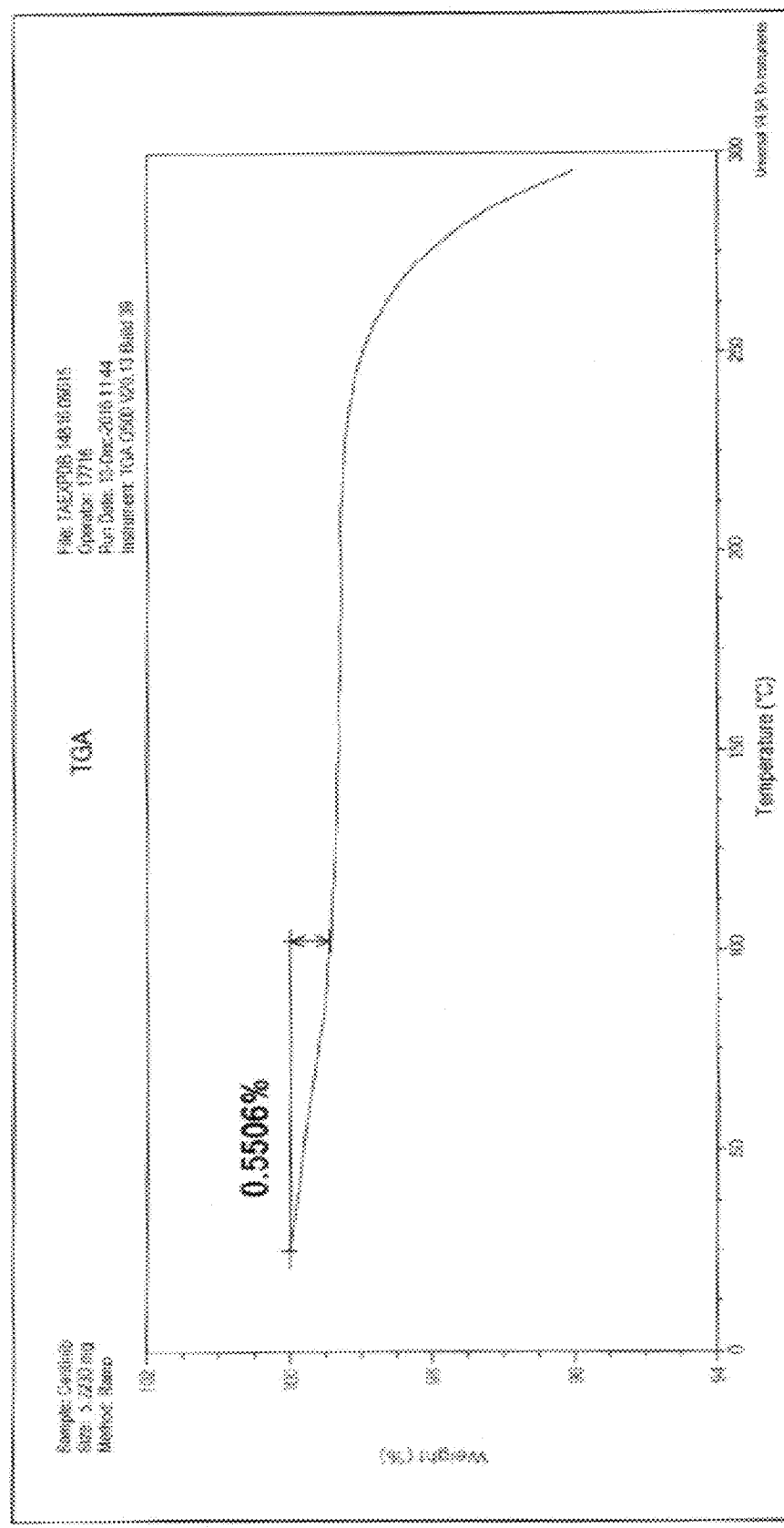
Fig-4: Thermogravimetric analysis (TGA) of an amorphous form of Ceritinib.

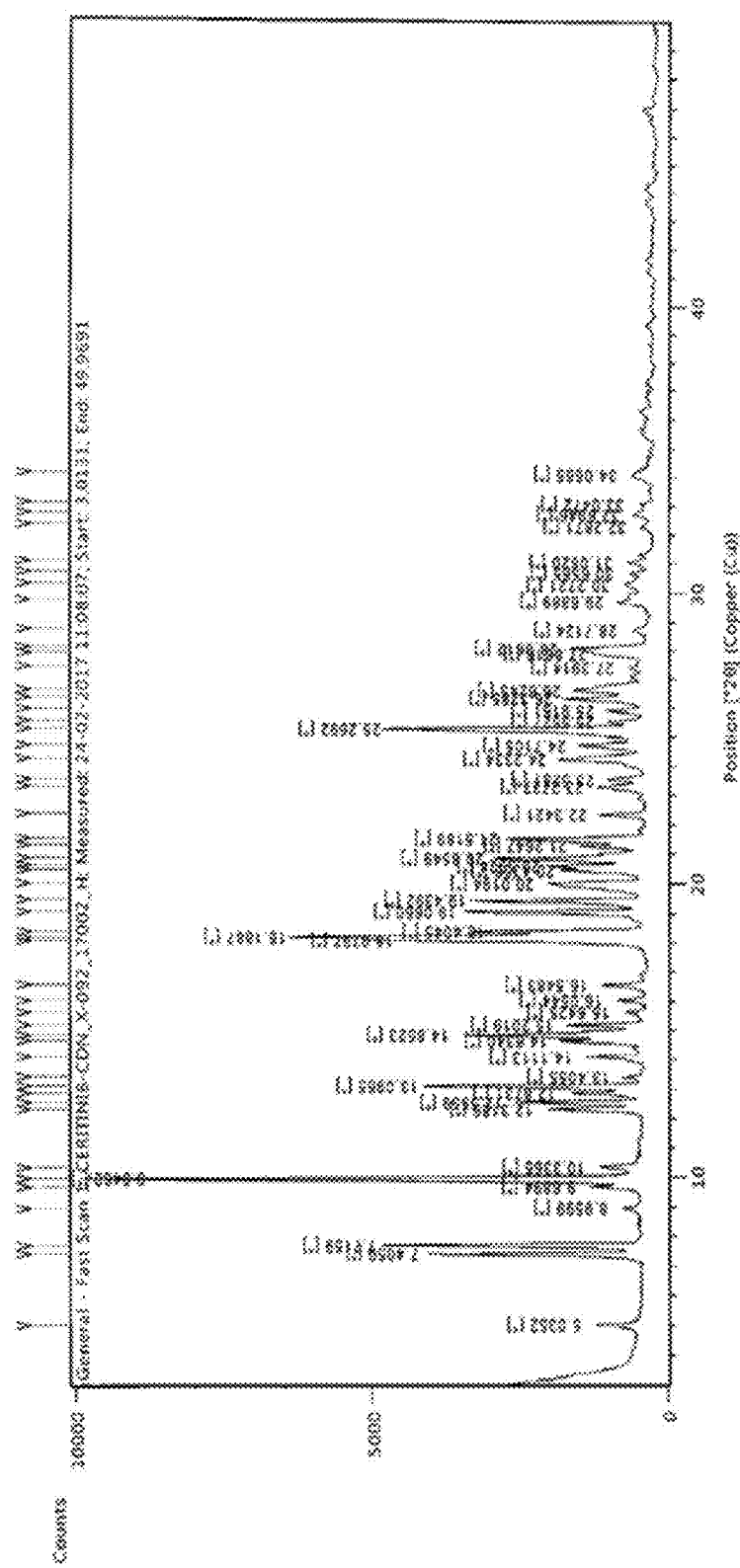
Fig-5: Powder X-ray diffractogram of toluene solvate of ceritinib.

MODIFIED PROCESS FOR THE PREPARATION OF CERITINIB AND AMORPHOUS FORM OF CERITINIB

FIELD OF THE INVENTION

The present invention is related to an improved process for the preparation of Ceritinib with high purity and high yields. The present invention also relates to a stable amorphous polymorphic form of Ceritinib and its preparation. The present invention also relates to a process for the preparation of Crystalline form A of Ceritinib.

BACKGROUND OF THE INVENTION

Ceritinib is a kinase inhibitor indicated for the treatment of patients with anaplastic lymphoma kinase (ALK)-positive metastatic non-small cell lung cancer (NSCLC).

Ceritinib is chemically known as 5-Chloro-N4-[2-[(1-methylethyl) sulfonyl]phenyl]-N2-[5-methyl-2-(1-methylethoxy)-4-(4-piperidinyl)phenyl]-2,4-pyrimidinediamine and structurally represented as below.

Formula I

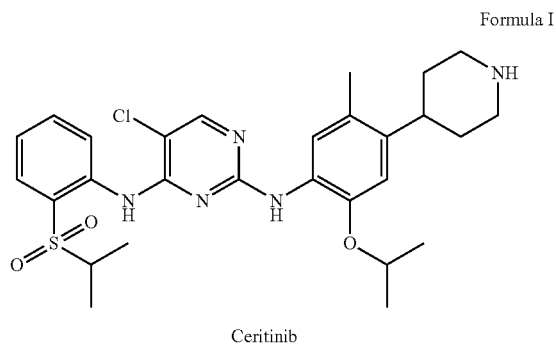 [SMILES: Cc1cc(Nc2ncc(Cl)c(Nc3ccccc3S(=O)(=O)C(C)C)n2)c(OC(C)C)cc1C1CCNCC1]

Ceritinib

Ceritinib was disclosed in U.S. Pat. No. 8,039,479 and marketed as ZYKADIA®. US'479 patent disclosed preparation of ceritinib, wherein 2,4,5-trichloro-pyrimidine (XII) is reacted with 2-(isopropylsulfonyl) aniline (XI) to get 2,5-dichloro-N-(2-(isopropyl sulfonyl)phenyl)pyrimidin-4-amine (XIII) and 4-pyridine boronic acid is reacted with 2-chloro-4-isopropoxy-5-nitro-toulene to get 4-(5-isopropoxy-2-methyl-4-nitro-phenyl)-pyridine (XVI), then it is treated with TFA and $PtO_2$ the reaction mixture was stirred and concentrated after workup to get residue. After concentration the crude was dissolved in dichloromethane and TEA and $Boc_2O$ was added to get 4-(4-amino-5-isopropoxy-2-methyl-phenyl)-piperidine-1-carboxylic acid tert-butyl ester (XVII).

2,5-dichloro-N-(2-(isopropyl sulfonyl)phenyl)pyrimidin-4-amine (XIII) and 4-(4-amino-5-isopropoxy-2-methyl-phenyl)-piperidine-1-carboxylic acid tert-butyl ester (XVII) were reacted in presence of palladium acetate and $Cs_2CO_3$ in THF solvent in a sealed reaction vessel heated with microwave irradiation. After concentration the crude product was purified by silica gel chromatography to give boc protected Ceritinib and this product was dissolved in dichloromethane and TFA and HCl is added causing the product HCl salt to precipitate. The schematic representation is as shown in below scheme-1.

Scheme-I

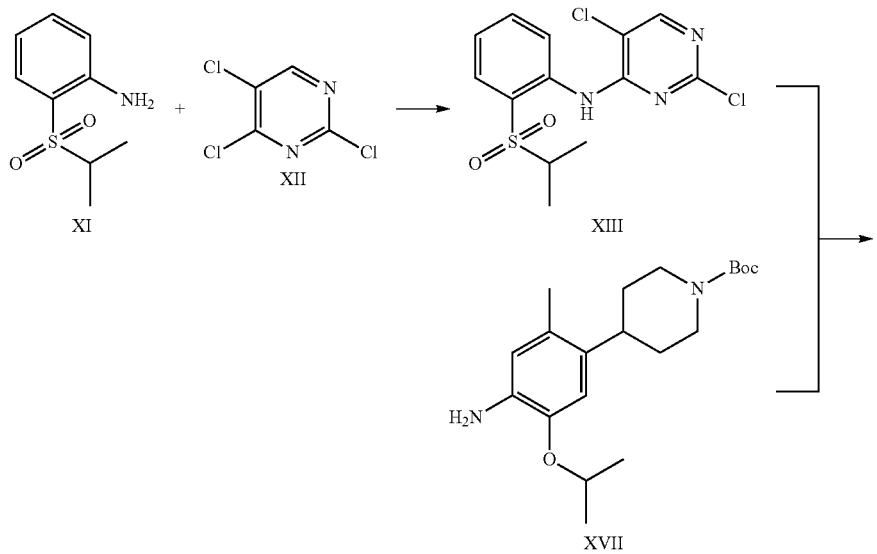

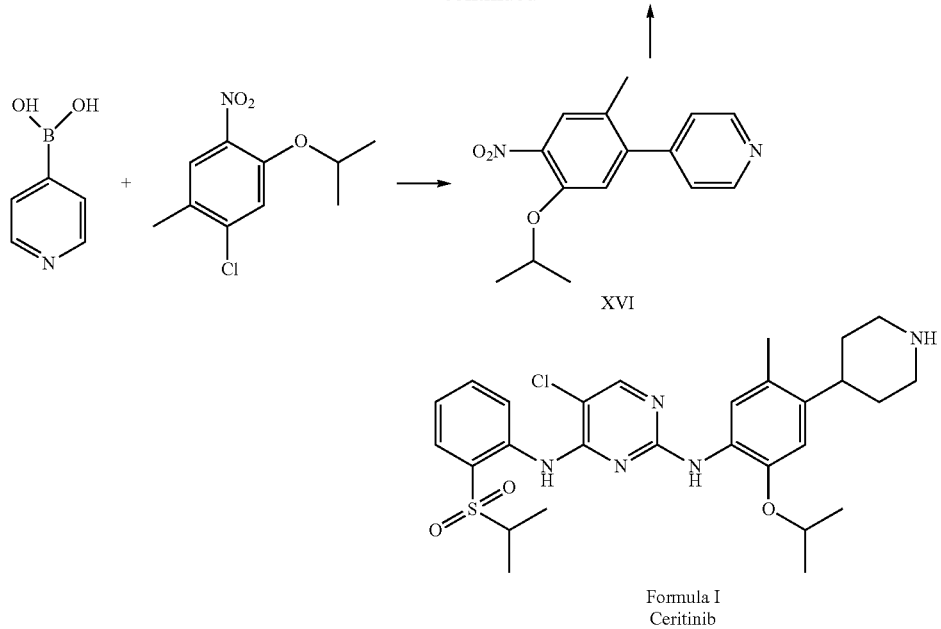

Formula I
Ceritinib

U.S. Pat. No. 9,309,229 discloses the crystalline form A and B of ceritinib. Wherein form A was prepared by reacting 2-isopropoxy-5-methyl-4-(piperdin-4-yl) aniline dihydrochloride and 2,5-dichloro-N-(2-(isopropyl sulfonyl)phenyl) pyrimidin-4-amine in presence of 2-propanol and the mixture was heated to get 5-chloro-N-(2-isopropoxy-5-methyl-4-(piperidin-4-ylphenyl)-N-2-(isopropylsulfonyl)phenyl)-2,4-diamine di-hydrochloride and this dihydrochloride salt was recrystallized using acetone:water.

Further to 5-chloro-N-(2-isopropoxy-5-methyl-4-(piperidin-4-yl)phenyl)-N-2-(isopropyl sulfonyl)phenyl)-2,4-diamine di-hydrochloride, acetone:water (3:1, v/v) was added at ambient temperature. The mixture was heated to 55±3° C. in about 20 minutes to obtain a clear solution. The hot solution was filtered and acetone and water was added to the mixture. While heating was maintained, aqueous NaOH solution was added over a period and the reaction mixture was maintained at 55±3° C. for an additional 2 hours to yield an off-white slurry. The slurry was cooled to 20±3° C. over a period of about 45 minutes and deionized (DI) water was added over about 30 minutes and the off-white slurry was stirred at 20±3° C. for 1 hour. The slurry was filtered and rinsed with DI water. The wet cake was dried about 17 hours in a vacuum oven at 50±3° C. and 10 mbar under a N2 purge to yield form A of Ceritinib.

Wherein form B was prepared as Ceritinib was dissolved in HCl at 30-40° C. to afford a clear solution. NaOH was added to this clear solution dropwise over 20 minutes at 20-23° C. A cloudy mixture was obtained, which was heated with stirring at 40-42° C. for 2 hours and subsequently heated to 50-55° C. for 2 hours. The resulting slurry was cooled to room temperature and the slurry was filtered. The wet cake was washed with water and dried under vacuum to obtain form B of ceritinib.

The present inventors of the present invention has developed an improved process for the preparation of ceritinib with high yield and high purity. The present process is cost effective and feasible in large scale production also. The present invention also related to a stable amorphous form of Ceritinib and its preparation. The amorphous form of Ceritinib of the present invention is stable up to 180 days. The present invention also relates to a process for the preparation of Crystalline form A of Ceritinib.

SUMMARY OF THE PRESENT INVENTION

One aspect of the present invention is to provide a process for the preparation of ceritinib comprising the steps of:
  a) reacting 2-methyl-4-nitro-5-isopropxy-phenylboronic acid pinacol ester (formula IV) with (1-benzyl-3,6-dihydro-2H-pyridin-4-yl)trifluoromethane sulfonate (formula-VII) to get 1-benzyl-4-(5-isopropoxy-2-methyl-4-nitro-phenyl)-3,6-dihydro-2H-pyridine (formula-VIII),
  b) reducing the 1-benzyl-4-(5-isopropoxy-2-methyl-4-nitro-phenyl)-3,6-dihydro-2H-pyridine (formula-VIII) in presence of reducing agent to get 2-isopropoxy-5-methyl-4-(piperdin-4-yl) aniline dihydrochloride (formula-X),
  c) reacting the 2-isopropoxy-5-methyl-4-(piperdin-4-yl) aniline dihydrochloride [formula-X] with 2,5-dichloro-N-(2-(isopropyl sulfonyl)phenyl)pyrimidin-4-amine (formula-XIII) to get Ceritinib di-hydrochloride salt, and
  d) converting ceritinib dihydrochloride salt to ceritinib (formula-I).

Another aspect of the present invention is to provide a process for the preparation of ceritinib comprising the steps of:
  a) reacting 4-(1-benzyl-4-piperidyl)-2-isopropoxy-5-methyl-aniline (formula-IX) with 2,5-dichloro-N-(2-(isopropyl sulfonyl)phenyl)pyrimidin-4-amine (formula-XIII) to get N-2-[4-(1-benzyl-4-piperidyl)-2-isopropoxy-5-methyl-phenyl]-5-chloro-N4-(2-isopropylsulfonylphenyl)pyrimidine-2,4-diamine (formula-XV), and
  b) deprotecting the N2-[4-(1-benzyl-4-piperidyl)-2-isopropoxy-5-methyl-phenyl]-5-chloro-N4-(2-isopropylsulfonylphenyl)pyrimidine-2,4-diamine (formula-XV) to yield ceritinib (formula-I).

Yet another aspect of the present invention is to provide a stable amorphous form of Ceritinib.

Yet another aspect of the present invention is to provide a process for the preparation of amorphous form ceritinib comprising the steps of:
a) treating Ceritinib dihydrochloride with acid or water,
b) adjusting the pH with base,
c) stirring the reaction mass at 25-35° C.,
d) optionally washing the mass with water, and
e) isolating the amorphous form of ceritinib.

Yet another aspect of the present invention is to provide a process for the preparation of crystalline form A of ceritinib comprising the steps of:
a) treating Ceritinib dihydrochloride with water and solvent or its mixture thereof,
b) adjusting the pH with base,
c) stirring the reaction mass at 25-35° C.,
d) optionally washing the mass with solvent, and
e) isolating the crystalline form A of Ceritinib.

Yet another aspect of the present invention is to provide a toluene solvate of Ceritinib.

DETAILED DESCRIPTION OF THE INVENTION

The present invention is related to an improved process for the preparation of Ceritinib. The present invention also relates to a stable amorphous form of Ceritinib. The present invention also relates to a process for the preparation of Crystalline form A of Ceritinib.

One embodiment of the present invention is to provide a process for the preparation of ceritinib comprising the steps of:
a) reacting 2-methyl-4-nitro-5-isopropxy-phenylboronic acid pinacol ester (formula IV) with (1-benzyl-3,6-dihydro-2H-pyridin-4-yl)trifluoromethane sulfonate (formula-VII) to get 1-benzyl-4-(5-isopropoxy-2-methyl-4-nitro-phenyl)-3,6-dihydro-2H-pyridine (formula-VIII),
b) reducing the 1-benzyl-4-(5-isopropoxy-2-methyl-4-nitro-phenyl)-3,6-dihydro-2H-pyridine (formula-VIII) in presence of reducing agent to get 2-isopropoxy-5-methyl-4-(piperdin-4-yl) aniline dihydrochloride (formula-X),
c) reacting the 2-isopropoxy-5-methyl-4-(piperdin-4-yl) aniline dihydrochloride [formula-X] with 2,5-dichloro-N-(2-(isopropyl sulfonyl)phenyl)pyrimidin-4-amine (formula-XIII) to get Ceritinib di-hydrochloride salt, and
d) converting ceritinib dihydrochloride salt to ceritinib (formula-I).

The present invention is shown in below scheme.

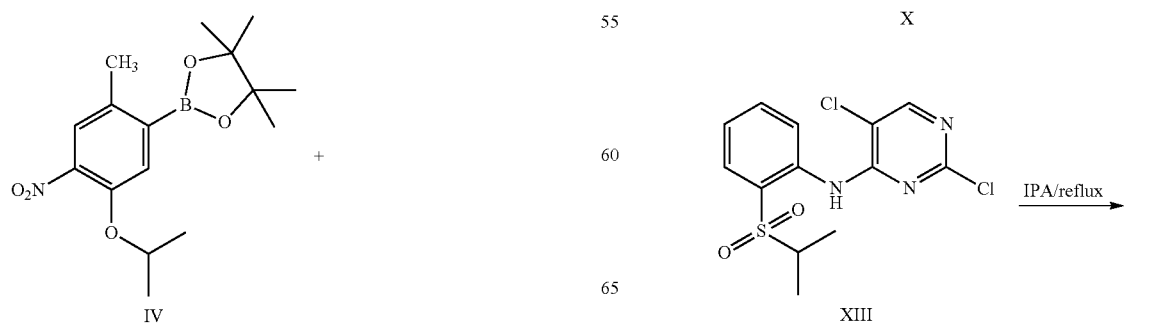

-continued

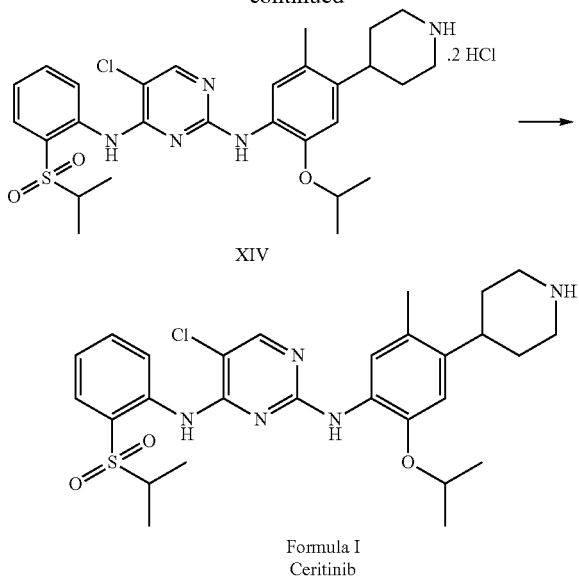

XIV

Formula I
Ceritinib

According to the present invention 2-methyl-4-nitro-5-isopropxy-phenylboronic acid pinacol ester (formula IV) with (1-benzyl-3,6-dihydro-2H-pyridin-4-yl)trifluoromethane sulfonate (formula-VII) in presence of triphenylphosphine and palladium(II) acetate aqueous and sodium bicarbonate solution is added, reaction mass temperature is raised to reflux after completion of reaction mass temperature is cooled to 25-30° C. and quenched the reaction mass with aqueous sodium bicarbonate solution. Reaction mass is extracted with ethyl acetate and added n-acetyl-1-cysteine solution and stirred for 20-30 min and dried over anhydrous sodium sulphate, and reaction mass is extracted with acetone by distillation under vacuum to give wet compound. Wet compound is dried to give 1-benzyl-4-(5-isopropoxy-2-methyl-4-nitro-phenyl)-3,6-dihydro-2H-pyridine (formula-VIII).

1-benzyl-4-(5-isopropoxy-2-methyl-4-nitro-phenyl)-3,6-dihydro-2H-pyridine (formula-VIII) is dissolved in methanol and solution is charged into a hydrogenator kettle. Charged 5% palladium on carbon with methanol suspension under nitrogen atmosphere. Fit the kettle to hydrogenator unit and feed the hydrogen gas upto 60-75 psi while maintaining the mass temperature 25-30° C. Feed the hydrogen gas upto gas consumption is stopped. After completion the reaction, filtered the catalyst under nitrogen atmosphere and kettle is washed with methanol. Methanol is removed by distillation under vacuum at a temperature 60° C. get the filtrate. And added isopropyl alcohol solution and raise the mass temperature up to 40-50° C., cooled the mass temperature to 0-5° C. Filtered the solid and washed with chilled isopropyl alcohol, dried compound under vacuum at 55-60° C. to give 2-isopropoxy-5-methyl-4-(piperdin-4-yl) aniline dihydrochloride (formula-X).

To a stirred suspension mass of 2-isopropoxy-5-methyl-4-(piperdin-4-yl) aniline dihydrochloride [formula-X] in isopropyl alcohol into a flask under nitrogen atmosphere. 2,5-dichloro-N-(2-(isopropyl sulfonyl)phenyl)pyrimidin-4-amine (formula-XIII) is added. Raised the reaction mass temperature to reflux under nitrogen and maintained for 35-40 hours. After completion of reaction, reaction mass is cooled to 25-30° C. and stirred the mass for 1 hour. Filtered the solid and washed the solid with isopropyl alcohol. The obtained solid is suspended in isopropyl alcohol into a flask. Raised the reaction mass temperature to reflux and maintained for 25-40 min. Reaction mas is cooled to 25-30° C. and stirred the mas for 30 min. Filtered the solid and washed the solid with isopropyl alcohol. The obtained solid is suspended in acetone into a flask. Raised the reaction mass temperature to reflux and maintained for 90-120 min. Reaction mas is cooled to 25-30° C. and filtered the solid and washed the solid with acetone. Dried the compound under vacuum at 55-60° C. to give 5-chloro-N2-(2-isopropoxy-5-methyl-4-(piperidin-4-ylphenyl)-N4-[2-(propane-2-sulfonyl)phenyl]pyrimidine-2,4-diamine di-hydrochloride salt [formula-XIV].

5-chloro-N-(2-isopropoxy-5-methyl-(piperidin-4-ylphenyl)-N-2-(isopropylsulfonyl)phenyl)-2,4-diamine di-hydrochloride salt (formula-XIV) and 0.1 N aqueous hydrochloride solution are charged into a flask. Stirred the mass for 5-15 min at 20-35° C. Reaction mass is formed to clear solution. Adjusted the mass pH to 9.1 with 1.0 N sodium hydroxide solution while maintaining the mass temperature at 20-35° C. Stirred the mass for 80-100 min at 20-35° C. Filtered the solid and washed with water. The wet compound is dried under vacuum at 55-60° C. to get Ceritinib (formula-I).

5-chloro-N-(2-isopropoxy-5-methyl-(piperidin-4-ylphenyl)-N-2-(isopropylsulfonyl)phenyl)-2,4-diamine di-hydrochloride salt (formula-XIV) and water are charged into a flask. Stirred the mass for 20-30 min at 20-35° C. Reaction mass is formed to clear solution. Adjusted the mass pH to 9 to 10 with 1.0 N aqueous ammonia solution while maintaining the mass temperature at 20-35° C. Stirred the mass for 30-45 min at 20-35° C. Filtered the solid and washed with water. The wet compound is dried under vacuum at 55-60° C. to get Ceritinib (formula-I).

Another embodiment of the present invention is to provide a process for the preparation of ceritinib comprising the steps of:
 a) reacting 4-(1-benzyl-4-piperidyl)-2-isopropoxy-5-methyl-aniline (formula-IX) with 2,5-dichloro-N-(2-(isopropyl sulfonyl)phenyl)pyrimidin-4-amine (formula-XIII) to get N2-[4-(1-benzyl-4-piperidyl)-2-isopropoxy-5-methyl-phenyl]-5-chloro-N4-(2-isopropylsulfonylphenyl)pyrimidine-2,4-diamine (formula-XV), and
 b) deprotecting the N2-[4-(1-benzyl-4-piperidyl)-2-isopropoxy-5-methyl-phenyl]-5-chloro-N4-(2-isopropylsulfonylphenyl)pyrimidine-2,4-diamine (formula-XV) to yield ceritinib (formula-I).

The present invention is shown in below scheme.

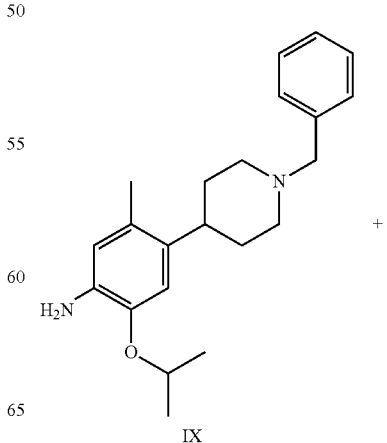

IX

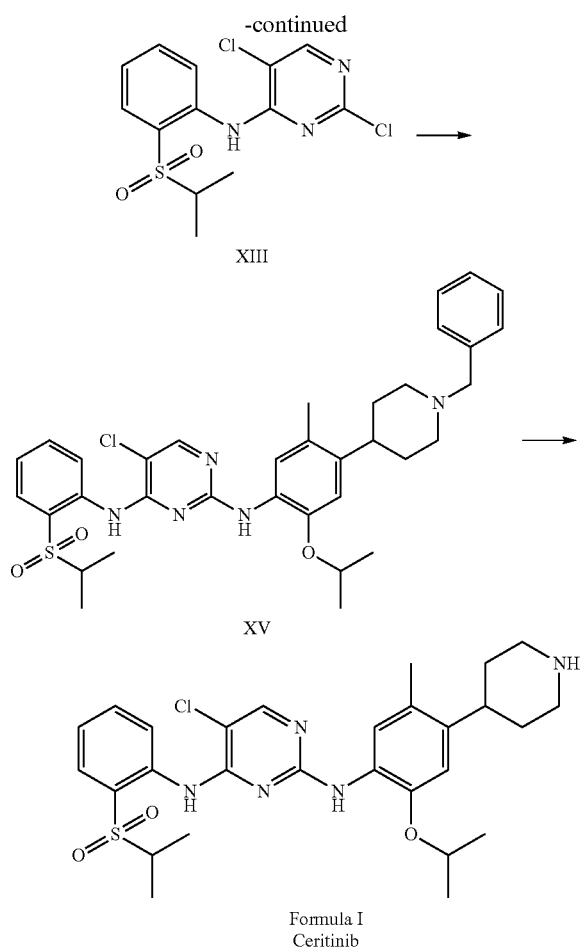

Formula I
Ceritinib

According to the present invention, 4-(1-benzyl-4-piperidyl)-2-isopropoxy-5-methyl-aniline (formula-IX) in isopropyl alcohol into a flask under nitrogen atmosphere 2,5-dichloro-N-(2-isopropyl sulfonyl)phenyl)pyrimidin-4-amine (formula-XIII) and para toluene sulfonic acid monohydrate were added to reaction mass. Reaction mass is heated to reflux temperature and maintained for 40 hours. Isopropyl alcohol is removed under vacuum and remaining mass is cooled to 25-30° C. Dichloromethane is added to remaining residual mass. Washed the mass with sodium bicarbonate solution and water. Organic layer is dried over anhydrous sodium sulphate. Dichloromethane is removed by distillation under vacuum at a temperature 60° C. to give crude compound. Crude oily mass is dissolved in acetone and adjusted the mass pH to 2.0 with isopropyl alcohol hydrochloride solution at 25-30° C. Stirred the mass for 1 hour. Filtered the solid and washed with acetone. Dried the compound under vacuum to give N2-[4-(1-benzyl-4-piperidyl)-2-isopropoxy-5-methyl-phenyl]-5-chloro-N4-(2-isopropylsulfonyl phenyl)pyrimidine-2,4-diamine (formula-XV). Further this compound is deprotected and converted to ceritinib.

Yet another embodiment of the present invention is to provide a stable amorphous form of Ceritinib.

According to the present invention, the obtained amorphous form of Ceritinib is stable up to 180 days. The stability of the amorphous form is confirmed by PXRD, DSC and TGA. The amorphous form of Ceritinib is highly pure and is stable towards polymorphic conversion.

Yet another embodiment of the present invention is to provide a process for the preparation of amorphous form ceritinib comprising the steps of:
a) treating ceritinib dihydrochloride with acid or water,
b) adjusting the pH with base,
c) stirring the reaction mass at 25-35° C.,
d) optionally washing the mass with water, and
e) isolating the amorphous form of ceritinib.

According to the present invention, 5-chloro-N-(2-isopropoxy-5-methyl-(piperidin-4-ylphenyl)-N-2-(isopropylsulfonyl)phenyl)-2,4-diamine di-hydrochloride salt and 0.1 N aqueous hydrochloride solution are charged into a flask. Stirred the mass for 5-15 min at 20-35° C. Reaction mass is formed to clear solution. Adjusted the mass pH to 9.1 with 1.0 N sodium hydroxide solution while maintaining the mass temperature at 20-35° C. Stirred the mass for 80-100 min at 20-35° C. Filtered the solid and washed with water. The wet compound is dried under vacuum at 55-60° C. to get amorphous form of ceritinib (formula-I).

5-chloro-N-(2-isopropoxy-5-methyl-(piperidin-4-ylphenyl)-N-2-(isopropylsulfonyl)phenyl)-2,4-diamine di-hydrochloride salt (formula-XIV) and water are charged into a flask. Stirred the mass for 20-30 min at 20-35° C. Reaction mass is formed to clear solution. Adjusted the mass pH to 9 to 10 with 1.0 N aqueous ammonia solution while maintaining the mass temperature at 20-35° C. Stirred the mass for 30-45 min at 20-35° C. Filtered the solid and washed with water. The wet compound is dried under vacuum at 55-60° C. to get amorphous form of Ceritinib (formula-I).

According to the present invention, reducing agent is selected form palladium on carbon, platinum oxide and raney nickel, preferably palladium on carbon.

According to the present invention, acid is selected from hydrochloric acid, acetic acid and sulfuric acid, preferably hydrochloric acid.

According to the present invention, base is selected from sodium hydroxide, ammonium hydroxide, ammonia and aqueous ammonia solution, preferably aqueous ammonia solution.

Accordingly to the present invention, the amorphous form of Ceritinib is highly pure and is free from the below impurities.

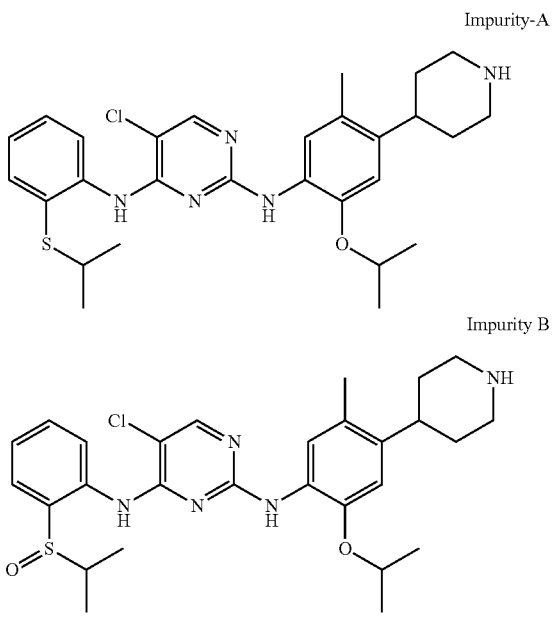

Impurity-A

Impurity B

-continued

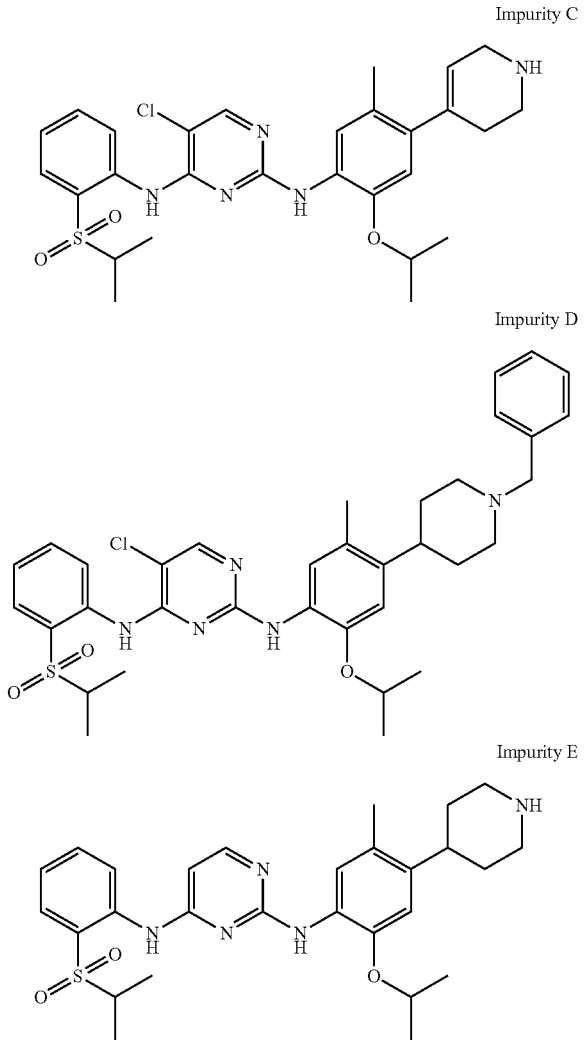

Impurity C

Impurity D

Impurity E

Yet another embodiment of the present invention is to provide a process for the preparation of crystalline form A of ceritinib comprising the steps of:
a) treating Ceritinib dihydrochloride with water and solvent or its mixture thereof,
b) adjusting the pH with base,
c) stirring the reaction mass at 25-35° C.,
d) optionally washing the mass with solvent, and
e) isolating the crystalline form A of Ceritinib.

According to the present invention, to a stirred solution of 5-chloro-N-(2-isopropoxy-5-methyl-(piperidin-4-ylphenyl)-N-2-(isopropylsulfonyl)phenyl)-2,4-diamine di-hydrochloride salt in water and solvent are added, raised the mass temperature to 50-60° C. Adjusted the mass pH to 9 to 10 with 1.0 N ammonium hydroxide solution while maintaining the mass temperature at 20-35° C. Stirred the mass for 80-100 min at 20-35° C. Filtered the solid and washed with solvent. The wet compound is dried under vacuum at 55-60° C. to get crystalline form A of ceritinib (formula-I).

According to the present invention, base is selected from sodium hydroxide, ammonium hydroxide, ammonia and aqueous ammonia solution, preferably aqueous ammonium hydroxide.

According to the present invention, solvent is selected from, isopropanol, methanol, ethanol, acetonitrile, preferably isopropanol.

Yet another embodiment of the present invention is to provide a toluene solvate of Ceritinib.

According to the present invention, to a stirred solution of 5-chloro-N-(2-isopropoxy-5-methyl-(piperidin-4-ylphenyl)-N-2-(isopropylsulfonyl)phenyl)-2,4-diamine di-hydrochloride salt in water. Adjusted the mass pH to 9 to 10 with 1.0 N ammonium hydroxide solution while maintaining the mass temperature at 20-35° C. Stirred the mass for 80-100 min at 20-35° C. Filtered the solid and washed with water to get wet compound. Toluene is added to the wet compound, raised the mass temperature to reflux and distilled the toluene, the solution is cooled to 25-30° C. for 60 min. filtered the solid and washed with toluene, the wet compound is dried under vacuum to get toluene solvate of Ceritinib.

BRIEF DESCRIPTION OF DRAWINGS

FIG. 1: Powder X-ray diffractogram of an amorphous form of ceritinib.
FIG. 2: Powder X-ray diffractogram of an amorphous form of ceritinib of 180 days
FIG. 3: Differential scanning calorimetry (DSC) pattern of an amorphous form of ceritinib
FIG. 4: Thermogravimetric analysis (TGA) of an amorphous form of ceritinib
FIG. 5: Powder X-ray diffractogram of toluene solvate of ceritinib The below examples are provided for illustrative purpose only and are not intended to limit the scope of invention.

EXPERIMENTAL SECTION

Example-1: Preparation of 2-methyl-4-nitro-5-isopropxy-phenylboronic acid pinacol ester

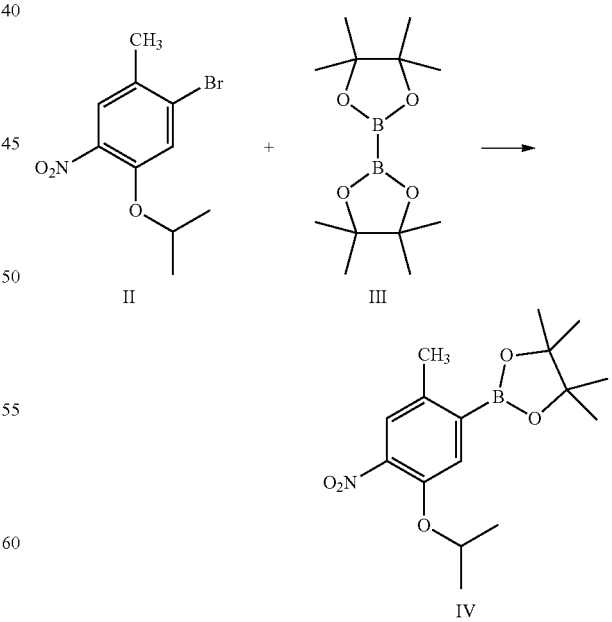

To a stirred solution of 50 g (0.182 mole) of 2-bromo-4-isopropoxy-5-nitrotoluene [formula-II] in 500 ml of isopropyl acetate into a flask under nitrogen atmosphere, 70 g (0.275 mole) of bis (pinacolato) diboron, 15 g (0.018 mole) of 1,1'-bis(diphenylphosphino)ferrocene dichloro palladium complex and 50.5 g (0.514 mole) of potassium acetate were added. Raised the reaction mass temperature to reflux and maintained for 3 hours. 2-bromo-4-isopropoxy-5-nitrotoluene was absent by TLC. Reaction mas was cooled to 25-30° C. and 250 ml of ethyl acetate was added and stirred for 15 min. Reaction mass was filtered and filter cake was washed with 250 ml of ethyl acetate. Filtrate was washed with two 375 ml portions of water, and dried over anhydrous sodium sulphate. Isopropyl acetate and ethyl acetate were removed by distillation under vacuum at a temperature 60° C. and cooled to 25-30° C. Crude mass was dissolved in 50 ml of hexane at reflux temperature. Mass was cooled to 25-30° C. and stirred for 30 min. Mass was further cooled to 0-5° C. and stirred the mass for 60 min. Solid was filtered and was dried under vacuum to give 40 g of 2-methyl-4-nitro-5-isopropxy-phenylboronic acid pinacol ester [formula-IV] light yellow coloured solid product with 68.2% yield by theory.

Example-2: Preparation of (1-benzyl-3,6-dihydro-2H-pyridin-4-yl)trifluoromethane sulfonate

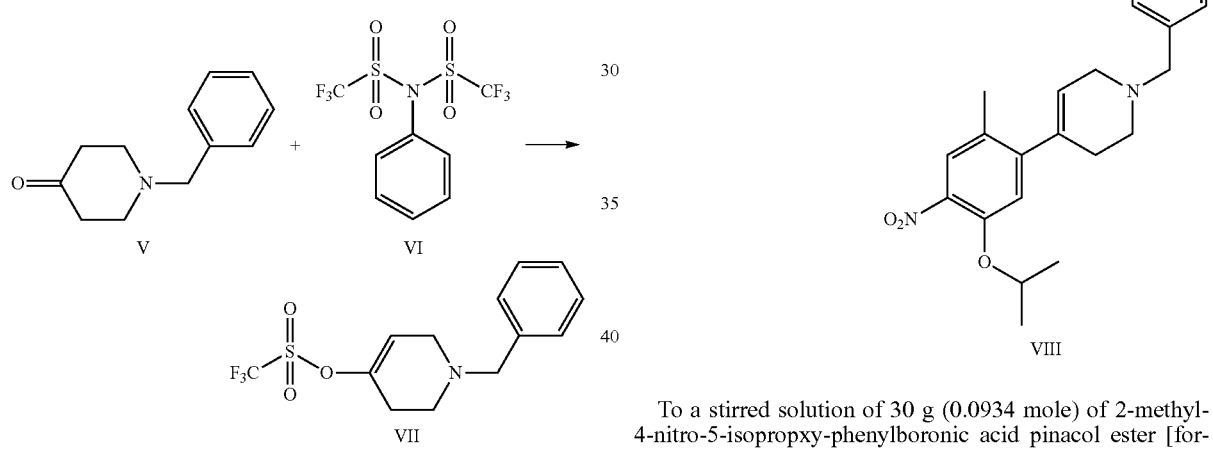

n-butyl lithium (198 ml, 0.316 mole, 1.6 molar in hexane) was added to a −78° C. solution of diisopropyl amine (0.328 mole) in tetrahydrofuran (60 ml). After 30 minutes, 1-benzyl-4-piperidone (formula-V) (50 g, 0.264 mole) in tetrahydrofuran (50 ml) was added slowly while maintaining the temperature at −75° C. to −80° C. The reaction mass was stirred at −75° C. to −80° C. for 1.5 hours, then n-phenyl-trifluoromethanesulfonimide (formula-VI) (103.8 g, 0.290 mole) in tetrahydrofuran (250 ml) was added slowly while maintaining the temperature at −75° C. to −80° C. The reaction mixture was allowed to warm to 25-30° C. Stirred the mass for 2 hours. 1-benzyl-4-piperidone was absent by TLC. Quenched the reaction mass in 500 ml of 20% aqueous ammonium chloride solution while maintaining the temperature below 5° C. Organic layer was separated and washed the organic layer with two portions of 250 ml of water. Organic layer was dried over anhydrous sodium sulphate, concentrated by distillation under vacuum at a temperature 60° C. to give 81.0 g of (1-benzyl-3,6-dihydro-2H-pyridin-4-yl)trifluoromethane sulfonate (formula-VII) as an oily mass with 95.3% yield by theory.

Example-3: Preparation of 1-benzyl-4-(5-isopropoxy-2-methyl-4-nitro-phenyl)-3,6-dihydro-2H-pyridine

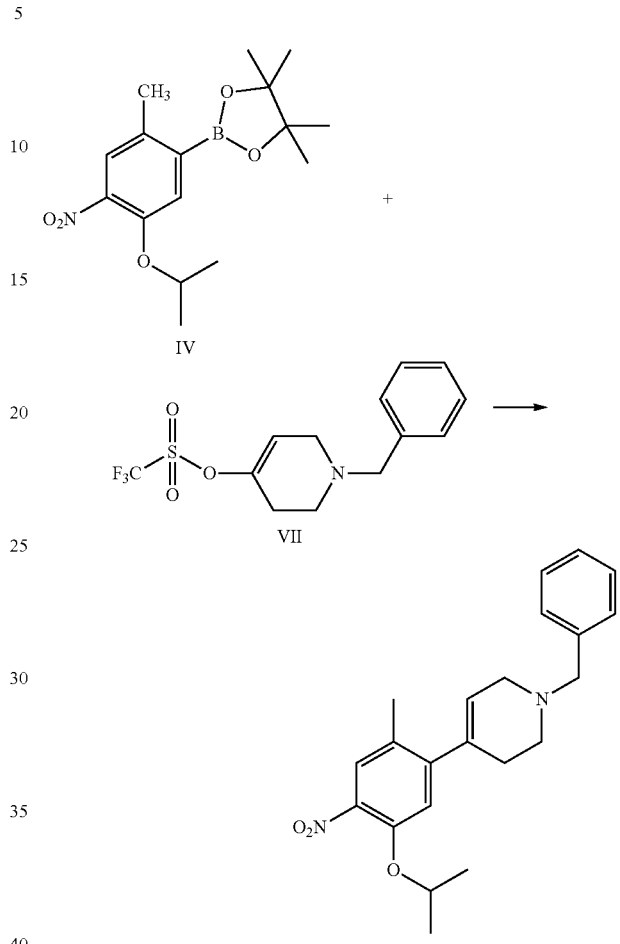

To a stirred solution of 30 g (0.0934 mole) of 2-methyl-4-nitro-5-isopropxy-phenylboronic acid pinacol ester [formula-IV] in 900 ml of 1,2-dimethoxyethane in a flask under nitrogen atmosphere, 57 g (0.177 mole) of (1-benzyl-3,6-dihydro-2H-pyridin-4-yl)trifluoromethane sulfonate (formula-VII), 4.2 g (0.018 mole) of triphenylphosphine, 2.1 g (0.009 mole) of palladium(II)acetate, 375 ml of 8% aqueous sodium bicarbonate solution were added. Raised the reaction mass temperature to reflux under mild nitrogen purging and maintained for 4 hours. 2-methyl-4-nitro-5-isopropxy-phenylboronic acid pinacol ester [formula-IV] was absent by TLC. Reaction mas was cooled to 25-30° C. and quenched with 1500 ml of aqueous sodium bicarbonate solution. Reaction mass was extracted with 2×600 ml of ethyl acetate and added n-acetyl-1-cysteine solution (5 gm) and stirred for 20-30 min, and dried over anhydrous sodium sulphate, and reaction mass was extracted with acetone (50 ml) by distillation under vacuum to give wet compound. Wet compound was dried to give 20 g of 1-benzyl-4-(5-isopropoxy-2-methyl-4-nitro-phenyl)-3,6-dihydro-2H-pyridine [formula-VIII] with 58.4% yield by theory.

$^1$HNMR (400 MHz, CDCl$_3$) δ—Value (ppm): 1.35-1.36 (d, 6H), 2.23 (s, 3H), 2.35-2.36 (br, m, 2H), 2.70-2.73 (t, 2H), 3.17-3.18 (br, m, 2H), 3.68 (s, 2H), 4.54-4.63 (septet, 1H), 5.58 (s, 1H), 6.82 (s, 1H), 7.25-7.39 (m, 5H), 7.60 (s, 1H).

$^{13}$CNMR (400 MHz, CDCl$_3$) δ—Value (ppm): 18.79 (1C), 21.94 (2C), 30.29 (1C), 49.52 (1C), 52.59 (1C), 62.64 (1C), 72.74 (1C), 116.53 (1C), 124.93 (1C), 126.70 (1C), 127.26 (1C), 127.46 (1C), 128.31 (2C), 129.25 (2C), 136.00 (1C), 137.63 (1C), 139.24 (1C), 148.72 (1C), 149.26 (1C).

Mass: 367.24 [M+H]$^+$

Example-4: Preparation of 4-(1-benzyl-4-piperidyl)-2-isopropoxy-5-methyl-aniline $^{13}$CNMR (400 MHz, CDCl$_3$) δ—Value (ppm): 18.21 (1C), 22.09 (2C), 32.73 (2C), 37.31 (1C), 54.01 (2C), 62.59 (1C), 70.32 (1C), 112.51 (1C), 116.47 (1C), 126.75 (1C), 126.96 (1C), 128.05 (2C), 128.80 (2C), 131.83 (1C), 136.42 (1C), 138.60 (1C), 142.50 (1C).

Mass: 339.32 [M+H]$^+$

Example-5: Preparation of 2-isopropoxy-5-methyl-4-(piperdin-4-yl) aniline dihydrochloride

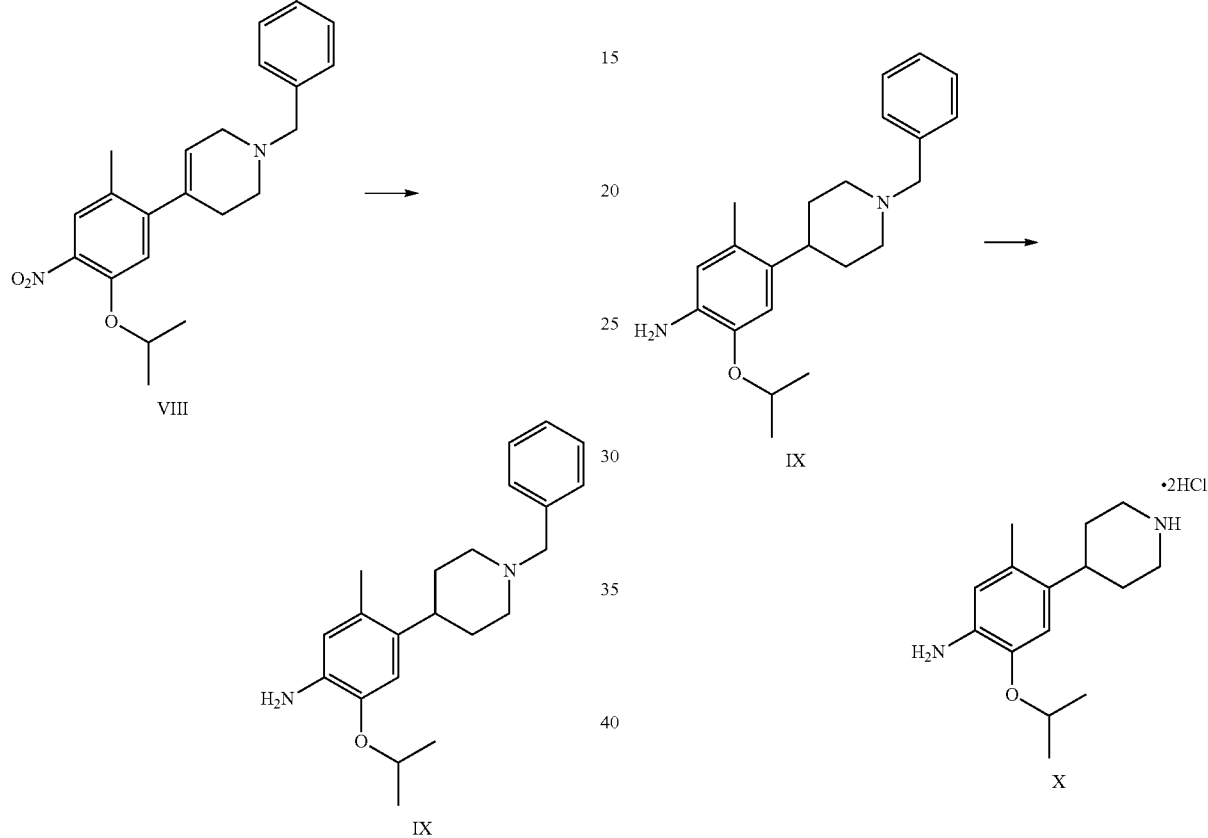

Dissolved 30 g (0.082 mole) of 1-benzyl-4-(5-isopropoxy-2-methyl-4-nitro-phenyl)-3,6-dihydro-2H-pyridine (formula-VIII) in 300 ml of methanol and solution was charged into a hydrogenator kettle. Charged 1.0 g (0.05 mole) of platinum (IV) oxide with 100 ml of methanol suspension under nitrogen atmosphere. Fit the kettle to hydrogenator unit and feed the hydrogen gas upto 60 psi while maintaining the mass temperature 25-30° C. Feed the hydrogen gas upto gas consumption was stopped. 1-benzyl-4-(5-isopropoxy-2-methyl-4-nitro-phenyl)-3,6-dihydro-2H-pyridine was absent by TLC. Filtered the catalyst under nitrogen atmosphere and kettle was washed with 200 ml of methanol. Methanol was removed by distillation under vacuum at a temperature 60° C. to give 26.4 g of 4-(1-benzyl-4-piperidyl)-2-isopropoxy-5-methyl-aniline of oily mass product with 95.5% yield by theory.

$^1$HNMR (400 MHz, CDCl$_3$) δ—Value (ppm): 1.21-1.23 (d, 6H), 1.56-1.59 (m, 4H), 1.98-2.06 (m, 2H), 2.08 (s, 3H), 2.44-2.49 (m, 2H), 2.87 (m, 1H), 3.47 (s, 2H), 4.34 (br, s, 2H), 4.36-4.44 (septet, 1H), 6.40 (s, 1H), 6.60 (s, 1H), 7.24-7.26 (m, 1H), 7.30-7.34 (m, 4H).

Dissolved 28.5 g (0.073 mole) of 4-(1-benzyl-4-piperidyl)-2-isopropoxy-5-methyl-aniline (formula-IX) in 400 ml of methanol and the solution was charged into a hydrogenator kettle. Charged 13 g of 5% palladium on carbon (50% wet) with 100 ml of methanol suspension under nitrogen atmosphere. Fit the kettle to hydrogenator unit and feed the hydrogen gas upto 65 psi while maintaining the mass temperature 25-30° C. Feed the hydrogen gas upto gas consumption is stopped. Checked the 4-(1-benzyl-4-piperidyl)-2-isopropoxy-5-methyl-aniline content by TLC. 4-(1-benzyl-4-piperidyl)-2-isopropoxy-5-methyl-aniline content is absent. Filtered the catalyst under nitrogen atmosphere and kettle was washed with 200 ml of methanol. Methanol was removed by distillation under vacuum at a temperature 60° C. to give 19.7 g of 2-isopropoxy-5-methyl-4-(piperdin-4-yl) aniline of oily mass product was obtained. The Oily mass obtained was dissolved in 350 ml of acetone and solution pH was adjusted to 1.6 with 71 ml of 15% isopropyl alcohol hydrochloride solution while maintaining the mass temperature at 25-30° C. Solid formation was observed. Solid mass stirred for 1 hour at 25-30° C. and cooled to 5-10° C. and maintained for 1 hour. Filtered the solid and washed with 150 ml of acetone. Dried compound under vacuum at 55-60° C. to give 18.3 g of 2-isopropoxy-5-methyl-4-(piperdin-4-yl) aniline dihydrochloride with 67.7% yield by theory.

Example-6: Preparation of 2-isopropoxy-5-methyl-4-(piperdin-4-yl) aniline dihydrochloride

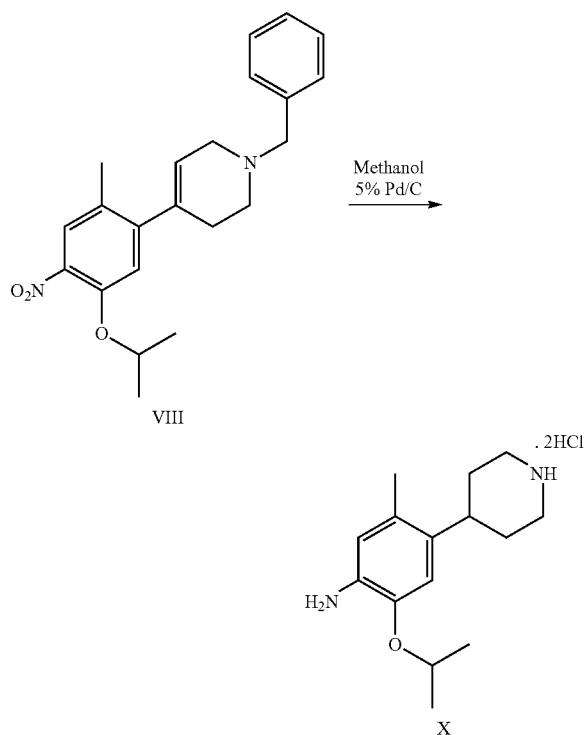

Dissolved 70 g of 1-benzyl-4-(5-isopropoxy-2-methyl-4-nitro-phenyl)-3,6-dihydro-2H-pyridine (formula-VIII) in 1100 ml of methanol and solution was charged into a hydrogenator kettle. Charged 35 g of palladium on carbon with 300 ml of methanol suspension under nitrogen atmosphere. Fit the kettle to hydrogenator unit and feed the hydrogen gas upto 60 psi while maintaining the mass temperature 25-30° C. Feed the hydrogen gas upto gas consumption is stopped. After the completion of the reaction, filtered the catalyst under nitrogen atmosphere and kettle was washed with 500 ml of methanol. Methanol was removed by distillation under vacuum at a temperature 60° C. to get the filtrate. And added 250 ml of isopropyl alcohol solution and raised the mass temperature up to 40-50° C., cooled the mass temperature to 0-5° C. Filtered the solid and washed with chilled isopropyl alcohol, dried compound under vacuum at 55-60° C. to give 26.4 g of 4-(1-benzyl-4-piperidyl)-2-isopropoxy-5-methyl-aniline product with 95.5% yield by theory.

Example-7: Preparation of 2,5-dichloro-N-(2-(isopropyl sulfonyl)phenyl)pyrimidin-4-amine

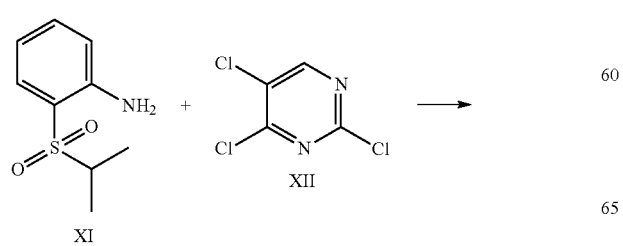

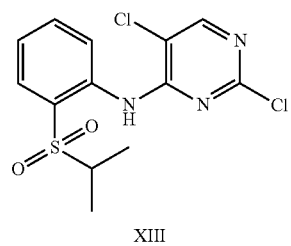

To a stirred solution of 40 g (0.200 mole) of 2-isopropyl-sulfonyl aniline [formula-XI] in 400 ml of toluene into a flask under nitrogen atmosphere. 49.7 g (0.27 mole) of 2,4,5-trichlropyrimidine (formula-XII), 81.7 g (0.25 mole) of caesium carbonate, 4.5 g (0.02 mole) of palladium(II) acetate, 13.1 g (0.05 mole) of triphenylphosphine were added. Raised the reaction mass temperature to reflux under nitrogen and maintained for 4 hours. Checked the TLC for 2-isopropylsulfonyl aniline content by TLC. 2-isopropylsulfonyl aniline content is absent. Reaction mass was cooled to 25-30° C. and filtered the mass. Washed the solid with 400 ml of ethyl acetate. Toluene and ethyl acetate were removed by distillation under vacuum at a temperature 60° C. to give crude compound. Crude compound was further purified by column chromotography to 45.6 g of 2,5-dichloro-N-(2-(isopropyl sulfonyl)phenyl)pyrimidin-4-amine [formula-XIII] as a light yellow solid product with 65.6% yield by theory.

Example-8: Preparation of 5-chloro-N2-(2-isopropoxy-5-methyl-4-(piperidin-4-yl)phenyl)-N4-[2-(propane-2-sulfonyl)phenyl]pyrimidine-2,4-diamine di-hydrochloride salt [Ceritinib di-hydrochloride salt)

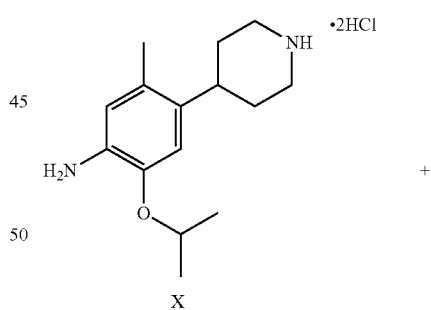

+

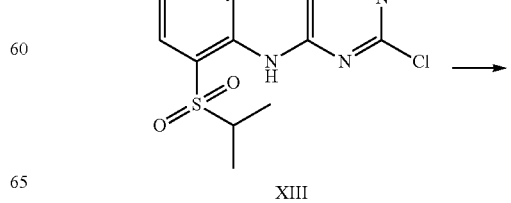

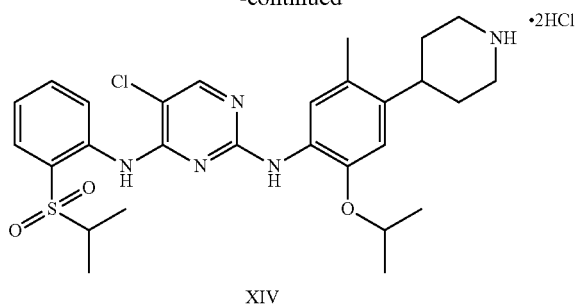

XIV

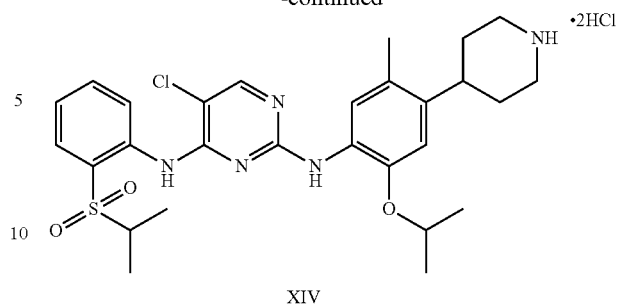

XIV

To a stirred solution of 50 g (0.182 mole) of 2-bromo-4-isopropoxy-5-nitrotoluene [formula-II] in 500 ml of isopropyl acetate into a flask under nitrogen atmosphere. 70 g (0.275 mole) of bis (pinacolato) diboron (formula III), 15 g (0.018 mole) of 1,1'-bis(diphenylphosphino)ferrocene dichloro palladium complex and 50.5 g (0.514 mole) of potassium acetate were added. Raised the reaction mass temperature to reflux and maintained for 3 hours. 2-bromo-4-isopropoxy-5-nitrotoluene was absent by TLC. Reaction mass was cooled to 25-30° C. and 250 ml of ethyl acetate was added and stirred for 15 min. Reaction mass was filtered, and filter cake was washed with 250 ml of ethyl acetate. Filtrate was washed with two 375 ml portions of water and dried over anhydrous sodium sulphate. Isopropyl acetate and ethyl acetate were removed by distillation under vacuum at a temperature 60° C. and cooled to 25-30° C. Crude mass was dissolved in 50 ml of hexane at reflux temperature. Mass was cooled to 25-30° C. and stirred for 30 min. Mass was further cooled to 0-5° C. and stirred the mass for 60 min. Solid was filtered and was dried under vacuum to give 40 g of 2-methyl-4-nitro-5-isopropoxy-phenylboronic acid pinacol ester [formula-IV] light yellow-colored solid product with 68.2% yield by theory.

Example-9: Preparation of 5-chloro-N2-(2-isopropoxy-5-methyl-4-(piperidin-4-ylphenyl)-N4-[2-(propane-2-sulfonyl)phenyl]pyrimidine-2,4-diamine di-hydrochloride salt [Ceritinib di-hydrochloride salt)

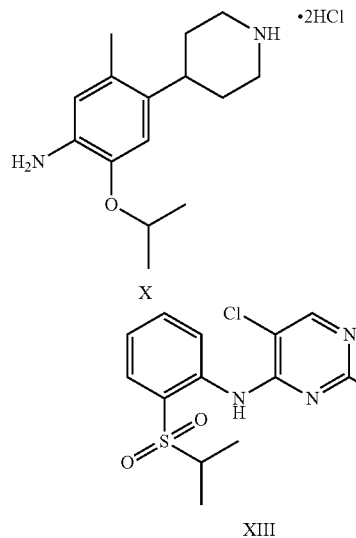

To a stirred suspension mass of 40 g of 2-isopropoxy-5-methyl-4-(piperdin-4-yl) aniline dihydrochloride [formula-X] in isopropyl alcohol into a flask under nitrogen atmosphere. 43 g of 2,5-dichloro-N-(2-(isopropyl sulfonyl) phenyl)pyrimidin-4-amine (formula-XIII) is added. Raised the reaction mass temperature to reflux under nitrogen and maintained for 35-40 hours. After the completion of reaction, reaction mass was cooled to 25-30° C. and stirred the mas for 1 hour. Filtered the solid and washed the solid with 100 ml of isopropyl alcohol. The obtained solid was suspended in 500 ml of isopropyl alcohol into a flask. Raised the reaction mass temperature to reflux and maintained for 25-40 min. Reaction mas was cooled to 25-30° C. and stirred the mas for 30 min. Filtered the solid and washed the solid with isopropyl alcohol. The obtained solid was suspended in 60 ml of acetone into a flask. Raised the reaction mass temperature to reflux and maintained for 90-120 min. Reaction mas is cooled to 25-30° C. and filtered the solid and washed the solid with acetone.

Example-10: Preparation of Stable Amorphous Form of 5-chloro-N2-(2-isopropoxy-5-methyl-4-(piperidin-4-ylphenyl)-N4-[2-(propane-2-sulfonyl)phenyl]pyrimidine-2,4-diamine [Ceritinib]

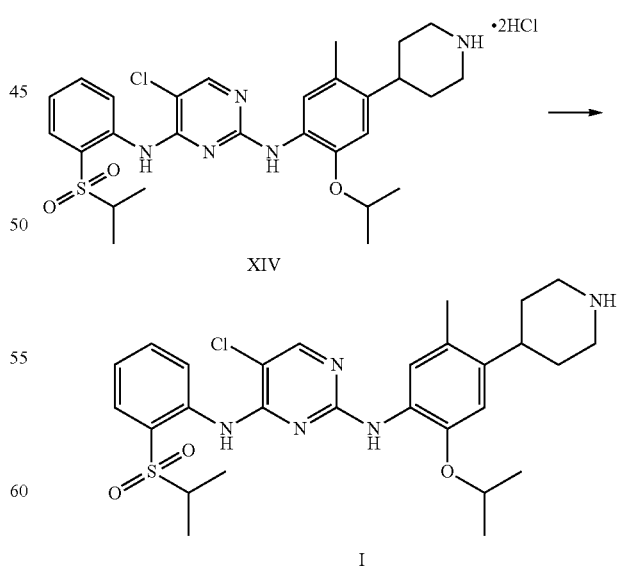

26.8 g (0.042 mole) of 5-chloro-N-(2-isopropoxy-5-methyl-(piperidin-4-ylphenyl)-N-2-(isopropylsulfonyl)phenyl)-2,4-diamine di-hydrochloride salt (formula-XIV) and 405 ml of 0.1 N aqueous hydrochloride solution were charged into a flask. Stirred the mass for 10 min at 25-30° C. Reaction mass was formed to clear solution. Adjusted the mass pH to 9.1 with 1.0 N sodium hydroxide solution while maintaining the mass temperature at 25-30° C. Stirred the mass for 90 min at 25-30° C. Filtered the solid and washed with 120 ml of water. The wet compound was dried under vacuum at 55-60° C. for 6 hours to give 16.8 g of 5-chloro-N2-(2-isopropoxy-5-methyl-4-(piperidin-4-ylphenyl)-N4-[2-(propane-2-sulfonyl)phenyl]pyrimidine-2,4-diamine [Ceritinib] amorphous form with 71% yield by theory.

Example-11: Preparation of Stable Amorphous Form of 5-chloro-N2-(2-isopropoxy-5-methyl-4-(piperidin-4-ylphenyl)-N4-[2-(propane-2-sulfonyl)phenyl]pyrimidine-2,4-diamine [Ceritinib]

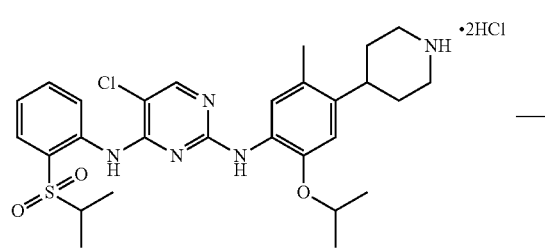

40 gm of 5-chloro-N-(2-isopropoxy-5-methyl-(piperidin-4-ylphenyl)-N-2-(isopropylsulfonyl)phenyl)-2,4-diamine di-hydrochloride salt (formula-XIV) and 1200 ml of water are charged into a flask. Stirred the mass for 20-30 min at 20-35° C. Reaction mass was formed to clear solution. Adjusted the mass pH to 9 to 10 with 1.0 N aqueous ammonia solution while maintaining the mass temperature at 20-35° C. Stirred the mass for 30-45 min at 20-35° C. Filtered the solid and washed with water. The wet compound was dried under vacuum at 55-60° C. to give 35 gm of 5-chloro-N2-(2-isopropoxy-5-methyl-4-(piperidin-4-ylphenyl)-N4-[2-(propane-2-sulfonyl)phenyl]pyrimidine-2,4-diamine [Ceritinib] amorphous form with 80% yield by theory.

Example-12: Preparation of N2-[4-(1-benzyl-4-piperidyl)-2-isopropoxy-5-methyl-phenyl]-5-chloro-N4-(2-isopropylsulfonylphenyl)pyrimidine-2,4-diamine

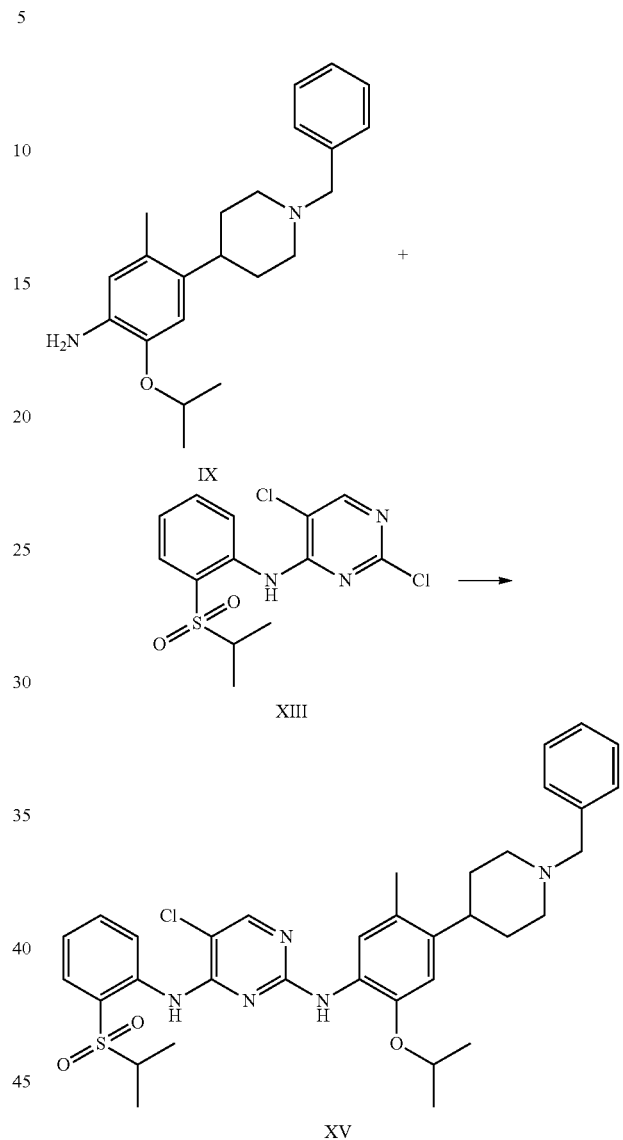

To a stirred solution of 8.0 g (0.236 mole) 4-(1-benzyl-4-piperidyl)-2-isopropoxy-5-methyl-aniline (formula-IX) in 160 ml of isopropyl alcohol in a flask under nitrogen atmosphere. 8.18 g (0.0236 mole) 2,5-dichloro-N-(2-(isopropyl sulfonyl)phenyl)pyrimidin-4-amine (formula-XIII) and 4.50 g (0.0236 mole) of para toluene sulfonic acid monohydrate were added. Reaction mass was heated to reflux temperature and maintained for 40 hours. Isopropyl alcohol was removed by distillation under vacuum and remaining mass was cooled to 25-30° C. 300 ml of methylene chloride was added to remaining residual mass. Washed the mass with 3×100 ml of 5% sodium bicarbonate solution and 100 ml of water. Organic layer was dried over anhydrous sodium sulphate. Methylene chloride was removed by distillation under vacuum to give crude compound. Crude oily mass was dissolved in 200 ml of acetone and adjusted the mass pH to 2.0 with isopropyl alcohol hydrochloride solution at 25-30° C. Stirred the mass for 1 hour. Filtered the solid and washed with 20 ml of acetone. Dried the compound under vacuum to give 6.30 g of N2-[4-(1-benzyl-4-piperidyl)-2-isopropoxy-5-methyl-phenyl]-5-chloro-N4-(2-isopropylsulfonylphenyl)pyrimidine-2,4-diamine (formula-XV) with 42.0% yield by theory.

Example-13: Preparation of Crystalline Form-A of 5-chloro-N2-(2-isopropoxy-5-methyl-4-(piperidin-4-ylphenyl)-N4-[2-(propane-2-sulfonyl)phenyl]pyrimidine-2,4-diamine [Ceritinib]

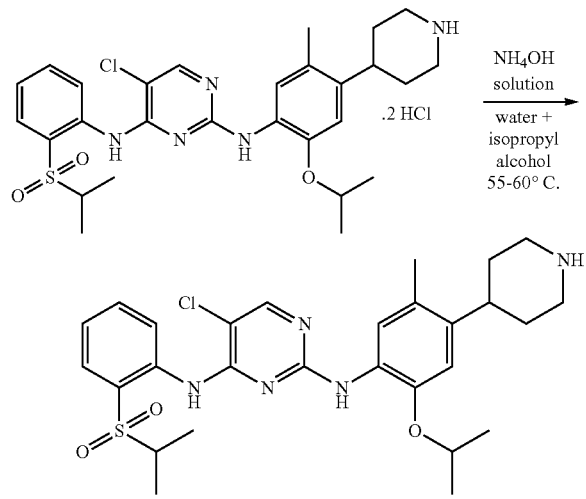

To a stirred solution of 10 g (0.0158 mole) of 5-chloro-N-(2-isopropoxy-5-methyl-(piperidin-4-ylphenyl)-N-2-(isopropylsulfonyl)phenyl)-2,4-diamine di-hydrochloride in 300 ml of purified water and 80 ml of isopropyl alcohol. Filtered the solution for free of foreign particles and washed the flask and funnel with 80 ml of purified and 20 ml of isopropyl alcohol mixed solution. Raised the mass temperature to 55-60° C. Adjusted the mass pH to 9.7 with ammonium hydroxide solution while maintaining the mass temperature at 55-60° C. Freely movable solid formation was observed. Maintained the mass temperature at 55-60° C. Cooled the mass temperature to 25-30° C. Maintained the mass temperature at 25-30° C. for 2 hours. Filtered the solid and washed the solid with 60 ml of aqueous isopropyl alcohol solution (diluted 50 ml of purified water with 10 ml of isopropyl alcohol). The wet compound was dried under vacuum at 55-60° C. for 2 hours to give 8.1 g (91.62% yield) of 5-chloro-N2-(2-isopropoxy-5-methyl-4-(piperidin-4-ylphenyl)-N4-[2-(propane-2-sulfonyl)phenyl]pyrimidine-2,4-diamine [Ceritinib crystalline form-A] with 99.8% purity by HPLC. P-XRD spectra 2θ values are matched with Ceritinib form-A values.

Example-14: Preparation of Crystalline Form-A of 5-chloro-N2-(2-isopropoxy-5-methyl-4-(piperidin-4-ylphenyl)-N4-[2-(propane-2-sulfonyl)phenyl]pyrimidine-2,4-diamine [Ceritinib]

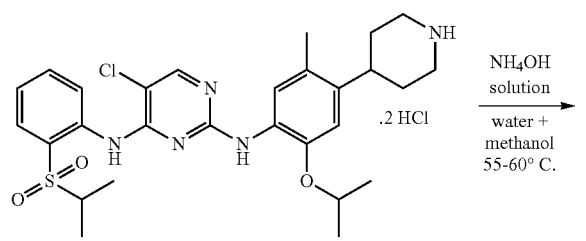

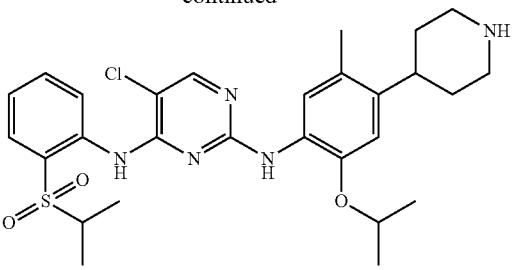

To a stirred solution of 2.5 g (0.0039 mole) of 5-chloro-N-(2-isopropoxy-5-methyl-(piperidin-4-ylphenyl)-N-2-(isopropylsulfonyl)phenyl)-2,4-diamine di-hydrochloride in 75 ml of purified water and 25 ml of isopropyl alcohol. Raised the mass temperature to 55-60° C. Adjusted the mass pH to 9.5 with ammonium hydroxide solution while maintaining the mass temperature at 55-60° C. Maintained the mass temperature at 55-60° C. for 1 hour. Cooled the mass temperature to 25-30° C. Maintained the mass temperature at 25-30° C. for 30 minutes. Filtered the solid by using Buchner funnel and Buchner flask under vacuum. Washed the solid with 12.5 ml of aqueous methanol solution (diluted 10 ml of purified water with 2.5 ml of methanol). The wet compound was dried under vacuum at 55-60° C. for 2 hours to give 1.9 g (86% yield) of 5-chloro-N2-(2-isopropoxy-5-methyl-4-(piperidin-4-ylphenyl)-N4-[2-(propane-2-sulfonyl)phenyl]pyrimidine-2,4-diamine [Ceritinib crystalline form-A] with 99.8% purity by HPLC. 2θ of P-XRD spectra are matched with Ceritinib form-A values.

Example-15: Preparation of Crystalline Form-A of 5-chloro-N2-(2-isopropoxy-5-methyl-4-(piperidin-4-ylphenyl)-N4-[2-(propane-2-sulfonyl)phenyl]pyrimidine-2,4-diamine [Ceritinib]

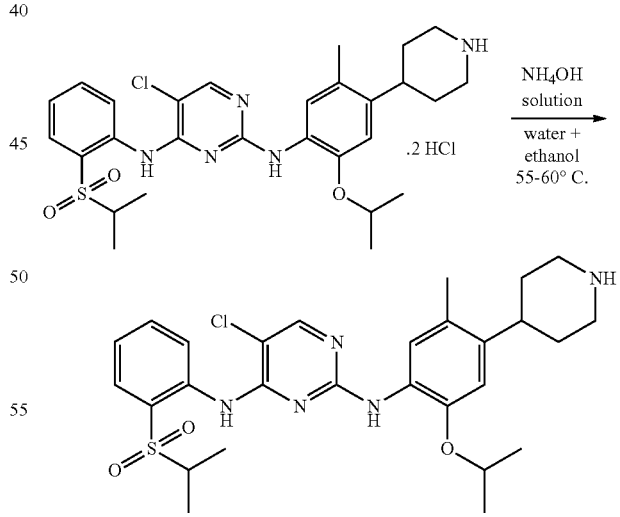

To a stirred solution of 2.5 g (0.0039 mole) of 5-chloro-N-(2-isopropoxy-5-methyl-(piperidin-4-ylphenyl)-N-2-(isopropylsulfonyl)phenyl)-2,4-diamine di-hydrochloride in 75 ml of purified water and 25 ml of ethanol. Raised the mass temperature to 55-60° C. Adjusted the mass pH to 10 with ammonium hydroxide solution while maintaining the mass temperature at 55-60° C. Maintained the mass temperature at 55-60° C. for 1 hour. Cooled the mass temperature to 25-30° C. Maintained the mass temperature at 25-30° C. for 30 minutes. Filtered the solid by using Buchner funnel and Buchner flask under vacuum. Washed the solid with 12.5 ml of aqueous ethanol solution (diluted 10 ml of purified water with 2.5 ml of ethanol). The wet compound was dried under vacuum at 55-60° C. for 2 hours to give 1.7 g (77% yield) of 5-chloro-N2-(2-isopropoxy-5-methyl-4-(piperidin-4-yl-phenyl)-N4-[2-(propane-2-sulfonyl)phenyl]pyrimidine-2,4-diamine [Ceritinib crystalline form-A] with 99.8% purity by HPLC. P-XRD spectra 2θ values are matching with Ceritinib form-A values.

Example-16: Preparation of Crystalline Form-A of 5-chloro-N2-(2-isopropoxy-5-methyl-4-(piperidin-4-ylphenyl)-N4-[2-(propane-2-sulfonyl)phenyl]pyrimidine-2,4-diamine [Ceritinib]

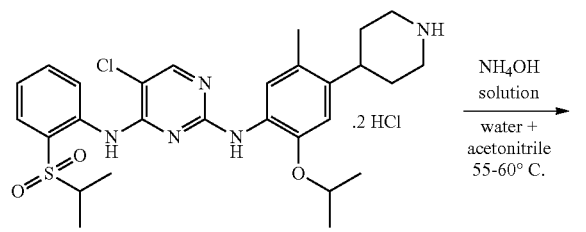

To a stirred solution of 2.5 g (0.0039 mole) of 5-chloro-N-(2-isopropoxy-5-methyl-(piperidin-4-ylphenyl)-N-2-(isopropylsulfonyl)phenyl)-2,4-diamine di-hydrochloride in 75 ml of purified water and 25 ml of acetonitrile. Raised the mass temperature to 55-60° C. Adjusted the mass pH to 10 with ammonium hydroxide solution while maintaining the mass temperature at 55-60° C. Maintained the mass temperature at 55-60° C. for 1 hour. Cooled the mass temperature to 25-30° C. Maintained the mass temperature at 25-30° C. for 30 minutes. Filtered the solid by using Buchner funnel and Buchner flask under vacuum. Washed the solid with 12.5 ml of aqueous acetonitrile solution (diluted 10 ml of purified water with 2.5 ml of acetonitrile). The wet compound was dried under vacuum at 55-60° C. for 2 hours to give 1.95 g (88.2% yield) of 5-chloro-N2-(2-isopropoxy-5-methyl-4-(piperidin-4-ylphenyl)-N4-[2-(propane-2-sulfonyl)phenyl]pyrimidine-2,4-diamine [Ceritinib crystalline form-A] with 99.8% purity by HPLC. P-XRD spectra 2θ values are matching with Ceritinib form-A values.

Example-17: Preparation of Crystalline Form-A of 5-chloro-N2-(2-isopropoxy-5-methyl-4-(piperidin-4-ylphenyl)-N4-[2-(propane-2-sulfonyl)phenyl]pyrimidine-2,4-diamine [Ceritinib]

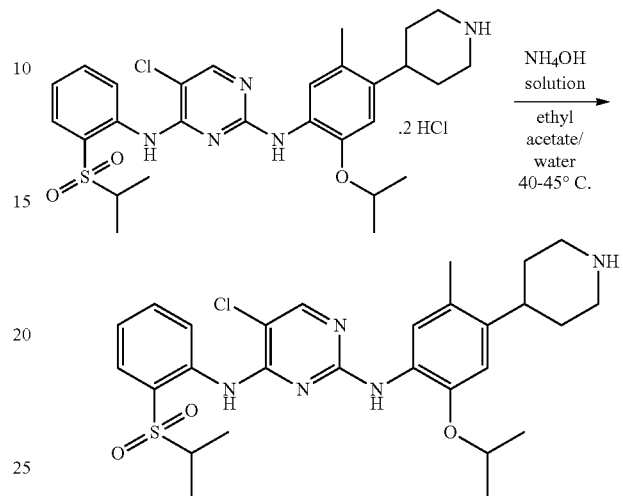

To a stirred solution of 2.5 g (0.0039 mole) of 5-chloro-N-(2-isopropoxy-5-methyl-(piperidin-4-ylphenyl)-N-2-(isopropylsulfonyl)phenyl)-2,4-diamine di-hydrochloride in 75 ml of purified water. Adjusted the mass pH to 10 with ammonium hydroxide solution while maintaining the mass temperature at 25-30° C. Maintained the mass temperature at 25-30° C. for 1 hour. Extracted the compound with 3×50 ml of ethyl acetate. Combined the organic layer and organic layer was dried with sodium sulphate. Filtered the sodium sulphate. Distilled of ethyl acetate completely under vacuum below 45° C. Remaining solid mass was suspended in 20 ml of ethyl acetate and stirred the mass for 30 minutes. Cooled the mass temperature to 25-30° C. Maintained the mass temperature at 25-30° C. for 30 minutes. Filtered the solid by using Buchner funnel and Buchner flask under vacuum. Washed the solid with 10 ml of ethyl acetate. The wet compound was dried under vacuum at 55-60° C. for 2 hours to give 1.45 g (65.6% yield) of 5-chloro-N2-(2-isopropoxy-5-methyl-4-(piperidin-4-ylphenyl)-N4-[2-(propane-2-sulfonyl)phenyl]pyrimidine-2,4-diamine [Ceritinib crystalline form-A] with 99.8% purity by HPLC. P-XRD spectra 2θ values are matching with Ceritinib form-A values.

Example-18: Preparation of Crystalline Form-A of 5-chloro-N2-(2-isopropoxy-5-methyl-4-(piperidin-4-ylphenyl)-N4-[2-(propane-2-sulfonyl)phenyl]pyrimidine-2,4-diamine [Ceritinib]

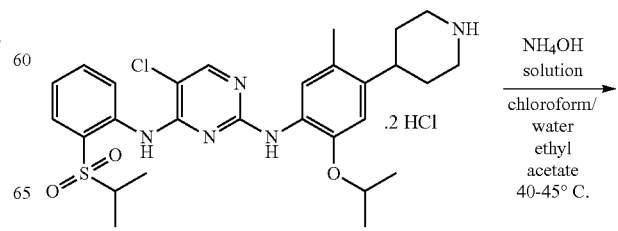

-continued

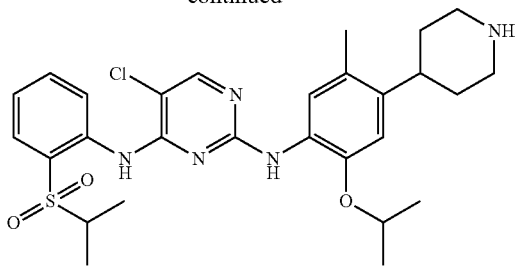

To a stirred solution of 2.5 g (0.0039 mole) of 5-chloro-N-(2-isopropoxy-5-methyl-(piperidin-4-ylphenyl)-N-2-(isopropylsulfonyl)phenyl)-2,4-diamine di-hydrochloride in 75 ml of purified water. Adjusted the mass pH to 10 with ammonium hydroxide solution while maintaining the mass temperature at 25-30° C. Maintained the mass temperature at 25-30° C. for 1 hour. Extracted the compound with 3×50 ml of chloroform. Combined the organic layer and organic layer was dried with sodium sulphate. Filtered the sodium sulphate. Distilled of chloroform completely under vacuum below 45° C. Remaining foamy solid mass was suspended in 20 ml of ethyl acetate and stirred the mass for 30 minutes at 25-30° C. Filtered the solid by using Buchner funnel and Buchner flask under vacuum. Washed the solid with 10 ml of ethyl acetate. The wet compound was dried under vacuum at 55-60° C. for 2 hours to give 1.50 g (67.8% yield) of 5-chloro-N2-(2-isopropoxy-5-methyl-4-(piperidin-4-ylphenyl)-N4-[2-(propane-2-sulfonyl)phenyl]pyrimidine-2,4-diamine [Ceritinib crystalline form-A] with 99.8% purity by HPLC. P-XRD spectra 2θ values are matching with Ceritinib form-A values.

Example-19: Preparation of Crystalline Form-A of 5-chloro-N2-(2-isopropoxy-5-methyl-4-(piperidin-4-ylphenyl)-N4-[2-(propane-2-sulfonyl)phenyl]pyrimidine-2,4-diamine [Ceritinib]

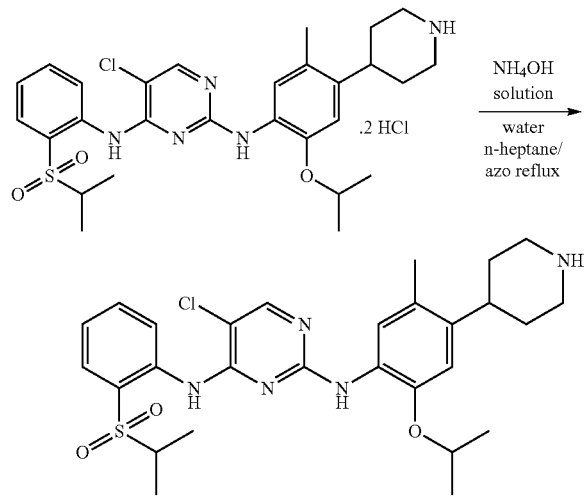

To a stirred solution of 2.5 g (0.0039 mole) of 5-chloro-N-(2-isopropoxy-5-methyl-(piperidin-4-ylphenyl)-N-2-(isopropylsulfonyl)phenyl)-2,4-diamine di-hydrochloride in 75 ml of purified water. Adjusted the mass pH to 9.8 with ammonium hydroxide solution while maintaining the mass temperature at 25-30° C. Maintained the mass temperature at 25-30° C. for 2 hour. Filtered the solid by using Buchner funnel and Buchner flask under vacuum. Washed the solid with 10 ml of purified water. 5.0 g of wet compound of was obtained. 5.0 g of wet compound and 100 ml of n-heptane were charged into a flask. Raised the mass temperature to azo reflux by dean stark apparatus. 2.2 ml of water was collected from dean stark apparatus. 50 ml of n-heptane was distilled by azo reflux. Remaining mass was cooled to 25-30° C. and maintained for 1 hour. Filtered the solid and washed with 10 ml of n-heptane. The wet compound was dried under vacuum at 55-60° C. for 3 hours to give 1.2 g (54.2% yield) of 5-chloro-N2-(2-isopropoxy-5-methyl-4-(piperidin-4-ylphenyl)-N4-[2-(propane-2-sulfonyl)phenyl] pyrimidine-2,4-diamine [Ceritinib form-A] with 99.8% purity by HPLC. P-XRD spectra 2θ values are matching with Ceritinib form-A values.

Example-20: Preparation of Crystalline Form-A of 5-chloro-N2-(2-isopropoxy-5-methyl-4-(piperidin-4-ylphenyl)-N4-[2-(propane-2-sulfonyl)phenyl]pyrimidine-2,4-diamine [Ceritinib]

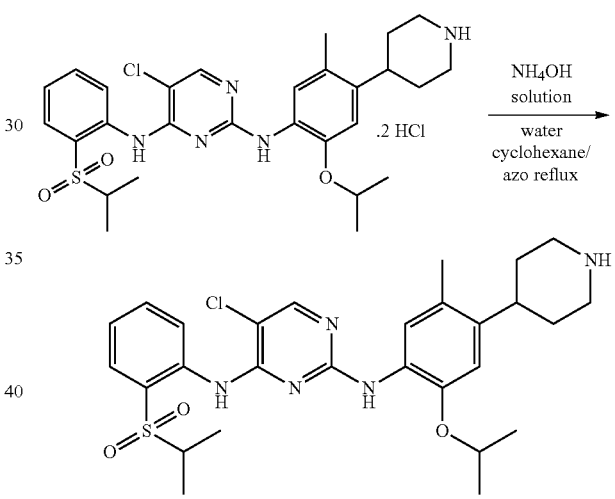

To a stirred solution of 2.5 g (0.0039 mole) of 5-chloro-N-(2-isopropoxy-5-methyl-(piperidin-4-ylphenyl)-N-2-(isopropylsulfonyl)phenyl)-2,4-diamine di-hydrochloride in 75 ml of purified water. Adjusted the mass pH to 9.8 with ammonium hydroxide solution while maintaining the mass temperature at 25-30° C. Maintained the mass temperature at 25-30° C. for 2 hour. Filtered the solid by using Buchner funnel and Buchner flask under vacuum. Washed the solid with 10 ml of purified water. 5.0 g of wet compound of was obtained. 5.0 g of wet compound and 100 ml of cyclohexane were charged into a flask. Raised the mass temperature to azo reflux by dean stark apparatus. 2.1 ml of water was collected from dean stark apparatus. 50 ml of cyclo hexane was distilled by azo reflux. Remaining mass was cooled to 25-30° C. and maintained for 1 hour. Filtered the solid and washed with 10 ml of cyclo hexane. The wet compound was dried under vacuum at 55-60° C. for 3 hours to give 1.0 g (45.4% yield) of 5-chloro-N2-(2-isopropoxy-5-methyl-4-(piperidin-4-ylphenyl)-N4-[2-(propane-2-sulfonyl)phenyl] pyrimidine-2,4-diamine [Ceritinib form-A] with 99.8% purity by HPLC. P-XRD spectra 2θ values are matching with Ceritinib form-A values.

Example-21: Preparation of Toluene Solvate of 5-chloro-N2-(2-isopropoxy-5-methyl-4-(piperidin-4-ylphenyl)-N4-[2-(propane-2-sulfonyl)phenyl]pyrimidine-2,4-diamine [Ceritinib]

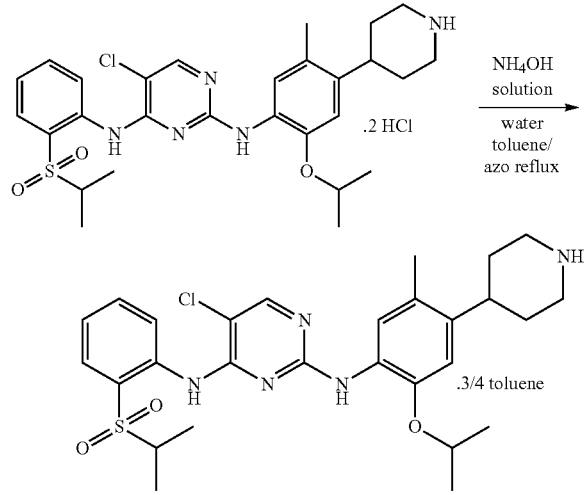

To a stirred solution of 3.0 g (0.0047 mole) of 5-chloro-N-(2-isopropoxy-5-methyl-(piperidin-4-ylphenyl)-N-2-(isopropylsulfonyl)phenyl)-2,4-diamine di-hydrochloride in 100 ml of purified water. Adjusted the mass pH to 9.8 with ammonium hydroxide solution while maintaining the mass temperature at 25-30° C. Maintained the mass temperature at 25-30° C. for 2 hour. Filtered the solid by using Buchner funnel and Buchner flask under vacuum. Washed the solid with 10 ml of purified water. 6.0 g of wet compound of was obtained. 6.0 g of wet compound and 60 ml of toluene were charged into a flask. Raised the mass temperature to azo reflux by dean stark apparatus. 2.6 ml of water was collected from dean stark apparatus. 30 ml of toluene was distilled by azo reflux. Remaining mass was cooled to 25-30° C. and maintained for 1 hour. Filtered the solid and washed with 10 ml of toluene. The wet compound was dried under vacuum at 55-60° C. for 3 hours to give 2.3 g (90.1% yield) of 5-chloro-N2-(2-isopropoxy-5-methyl-4-(piperidin-4-ylphenyl)-N4-[2-(propane-2-sulfonyl)phenyl]pyrimidine-2,4-diamine [Ceritinib toluene solvate form] with 99.8% purity by HPLC.

We claim:
1. A process for the preparation of Ceritinib comprising the steps of:
   a) reacting 2-methyl-4-nitro-5-isopropoxy-phenylboronic acid pinacol ester (formula IV) with (1-benzyl-3,6-dihydro-2H-pyridin-4-yl)trifluoromethane sulfonate (formula-VII) in the presence of a palladium complex and a base to produce 1-benzyl-4-(5-isopropoxy-2-methyl-4-nitro-phenyl)-3,6-dihydro-2H-pyridine (formula-VIII),
   b) reducing the 1-benzyl-4-(5-isopropoxy-2-methyl-4-nitro-phenyl)-3,6-dihydro-2H-pyridine (formula-VIII) in the presence of a reducing agent to produce 2-isopropoxy-5-methyl-4-(piperidin-4-yl) aniline dihydrochloride (formula-X),
   c) reacting the 2-isopropoxy-5-methyl-4-(piperidin-4-yl) aniline dihydrochloride (formula-X) with 2,5-dichloro-N-(2-(isopropyl sulfonyl)phenyl)pyrimidin-4-amine (formula-XIII) in solvent and under reflux to produce Ceritinib dihydrochloride salt (formula XIV), and
   d) converting the ceritinib dihydrochloride salt (formula XIV) into ceritinib in the presence of a base (formula-I)

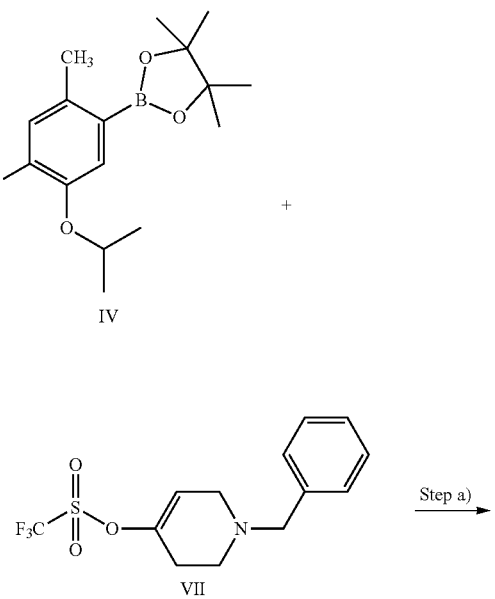

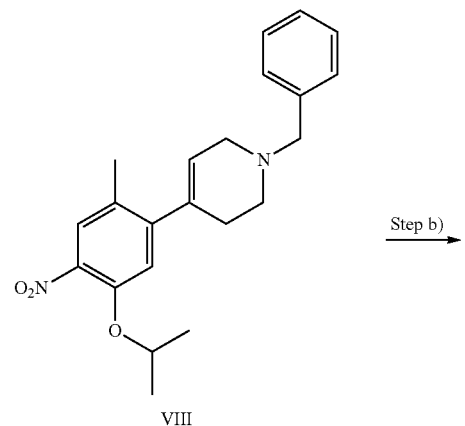

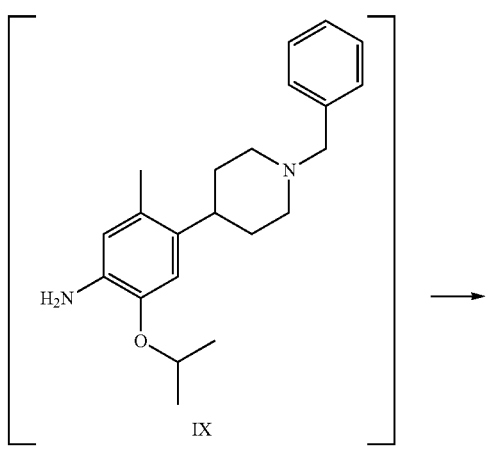

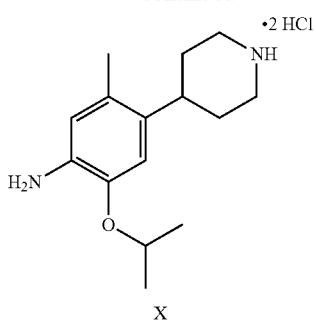

X

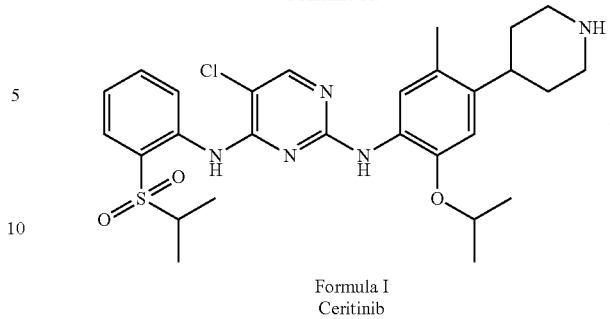

Formula I
Ceritinib

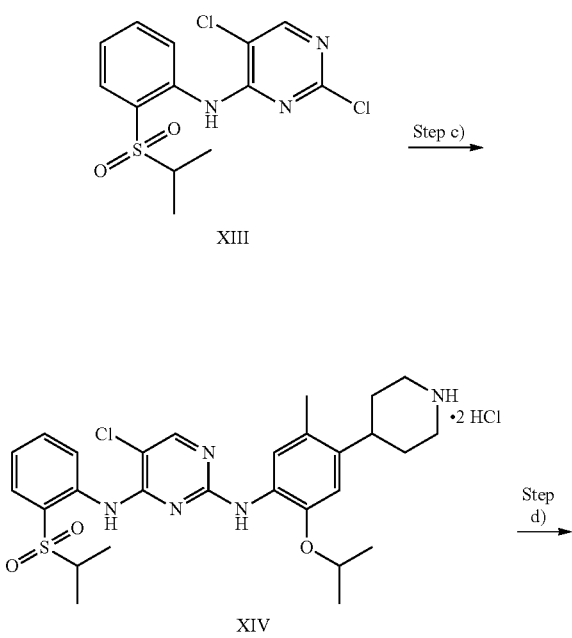

2. A process according to claim 1, wherein the reducing agent is selected from palladium on carbon, platinum oxide and raney nickel.

3. The process according to claim 1, wherein the Ceritinib is crystalline form A of Certinib, and wherein step (d) comprises a process for the preparation of crystalline form A of Ceritinib comprising the steps of:
   e) treating the Ceritinib dihydrochloride (formula XIV) obtained in step (c) with water, solvent or a mixture thereof, to form a reaction mass,
   f) adjusting the pH of the reaction mass obtained in step (e) with a base,
   g) stirring the reaction mass at 25-35° C., and
   h) isolating the crystalline form A of Ceritinib.

4. The process according to claim 3, wherein the base is selected from sodium hydroxide, ammonium hydroxide, ammonia and an aqueous ammonia solution.

5. The process according to claim 3, wherein the solvent is selected from isopropanol, methanol, ethanol and acetonitrile.

6. The process according to claim 3, further comprising a step of washing the reaction mass with a second solvent.

7. The process according to claim 1, wherein in step (b) an intermediate, 4-(1-benzyl-4-piperidyl)-2-isopropoxy-5-methyl-aniline (formula IX) is formed by reducing the 1-benzyl-4-(5-isopropoxy-2-methyl-4-nitro-phenyl)-3,6-dihydro-2H-pyridine (formula-VIII) in the presence of a reducing agent, and then the 4-(1-benzyl-4-piperidyl)-2-isopropoxy-5-methyl-aniline (formula IX) is further reduced into 2-isopropoxy-5-methyl-4-(piperidin-4-yl) aniline dihydrochloride (formula-X).

* * * * *